(12) United States Patent
Pinchman et al.

(10) Patent No.: US 11,339,103 B2
(45) Date of Patent: May 24, 2022

(54) CONTINUOUS FLOW PROCESSES FOR MAKING BICYCLIC COMPOUNDS

(71) Applicant: Recurium IP Holdings, LLC, San Diego, CA (US)

(72) Inventors: Joseph Robert Pinchman, San Diego, CA (US); Kevin Duane Bunker, Escondido, CA (US); Matthew M. Bio, Cambridge, MA (US); Christopher Breen, Cambridge, MA (US); Andrew M. Clausen, Cambridge, MA (US); Yuanqing Fang, Cambridge, MA (US); Hui Li, Cambridge, MA (US); Jillian W. Sheeran, Cambridge, MA (US)

(73) Assignee: RECURIUM IP HOLDINGS, LLC, San Diego, CA (US)

( * ) Notice: Subject to any disclaimer, the term of this patent is extended or adjusted under 35 U.S.C. 154(b) by 0 days.

(21) Appl. No.: 16/644,640

(22) PCT Filed: Sep. 6, 2018

(86) PCT No.: PCT/US2018/049680
§ 371 (c)(1),
(2) Date: Mar. 5, 2020

(87) PCT Pub. No.: WO2019/051038
PCT Pub. Date: Mar. 14, 2019

(65) Prior Publication Data
US 2021/0061730 A1    Mar. 4, 2021

Related U.S. Application Data

(60) Provisional application No. 62/556,897, filed on Sep. 11, 2017.

(51) Int. Cl.
*C07C 1/28* (2006.01)
*B01J 31/12* (2006.01)
(Continued)

(52) U.S. Cl.
CPC ............ *C07C 1/28* (2013.01); *B01J 19/002* (2013.01); *B01J 19/0053* (2013.01);
(Continued)

(58) Field of Classification Search
CPC ..................................................... C07C 13/605
See application file for complete search history.

(56) References Cited

U.S. PATENT DOCUMENTS

| 5,405,550 A | * | 4/1995 | Michl | ............. C07C 23/24 252/299.01 |
| 2016/0075654 A1 | * | 3/2016 | Bunker | ................. A61P 21/00 514/335 |
| 2017/0081295 A1 | | 3/2017 | Bunker | |

FOREIGN PATENT DOCUMENTS

| SU | 1509348 | 9/1989 |
| WO | WO 2015/089170 A1 | 6/2015 |

(Continued)

OTHER PUBLICATIONS

Makarov et al. "Synthesis of Bicyclo[1.1.1]pentane Bioisosteres of Internal Alkynes and para-Disubstituted Benzenes from [1.1.1] Propellane" Angew. Chem. Int. Ed. 2017, 56, 12774-12777 (Year: 2017).*

(Continued)

*Primary Examiner* — Philip Y Louie
(74) *Attorney, Agent, or Firm* — Knobbe Martens Olson & Bear LLP

(57) ABSTRACT

Processes for making bicyclic compounds and precursors thereof, and particularly for making [1.1.1]propellane and bicyclo[1.1.1]pentane and derivatives thereof, utilize continuous flow reaction methods and conditions. A continuous process for making [1.1.1]propellane can be conducted under reaction conditions that advantageously minimize (Continued)

clogging of a continuous flow reactor. A continuous flow process can be used to make precursors of [1.1.1]propellane.

31 Claims, 13 Drawing Sheets

(51) Int. Cl.

| | |
|---|---|
| *B01J 19/12* | (2006.01) |
| *B01J 19/00* | (2006.01) |
| *B01J 23/44* | (2006.01) |
| *B01J 23/755* | (2006.01) |
| *C07C 7/144* | (2006.01) |
| *C07C 209/02* | (2006.01) |
| *C07C 13/605* | (2006.01) |
| *C07C 211/38* | (2006.01) |

(52) U.S. Cl.
CPC ............ *B01J 19/123* (2013.01); *B01J 23/44* (2013.01); *B01J 23/755* (2013.01); *C07C 7/144* (2013.01); *C07C 209/02* (2013.01); *B01J 2219/00033* (2013.01); *B01J 2219/00051* (2013.01); *B01J 2219/00166* (2013.01); *C07C 13/605* (2013.01); *C07C 211/38* (2013.01); *C07C 2523/04* (2013.01); *C07C 2523/06* (2013.01); *C07C 2527/24* (2013.01); *C07C 2602/38* (2017.05); *C07C 2603/62* (2017.05)

(56) References Cited

FOREIGN PATENT DOCUMENTS

| | | | |
|---|---|---|---|
| WO | WO-2015134710 A1 * | 9/2015 | ........... C07C 255/64 |
| WO | WO 2017/157932 | 9/2017 | |
| WO | WO-2017157932 A1 * | 9/2017 | ........... C07C 231/12 |
| WO | WO 2017/172957 | 10/2017 | |
| WO | WO 2017/205459 | 11/2017 | |

OTHER PUBLICATIONS

Thakur et al. "Static Mixers in the Process Industries-A Review" Trans IChemE, vol. 81, Part A, Aug. 2003 (Year: 2003).*
Lopchuk et al. "Strain-Release Heteroatom Functionalization: Development, Scope, and Stereospecificity" JACS 2017, 139, 3209-3226 (Year: 2017).*
Kostikov et al. "Product Class 3:Cyclobutanes" from Science of Synthesis vol. 48 ISBN 9783131940919. 2009 (Year: 2009).*
Search Report dated Jan. 14, 2021 in Singaporean Patent Application No. 11202001733V filed Jun. 9, 2018.
Auberson, Dr. Yves P., et al., "Improving non-specific binding and solubility: bicycloalkyls and cubanes as p-phenyl bioisosteres", ChemMedChem, 2017, 1-10.
Ellioitt, Luke D., et al., "Batch versus Flow Photochemistry: A Revealing Comparison of Yield and Productivity", Chem. Eur. J. 2014, 20, 1-8.
Gianatassio, Ryan, et al., "Strain-release amination", Science, Jan. 15, 2016, vol. 351, Issue 6270, 241-246.
Lynch, Kathleen M. and William P. Dailey, "Improved Preparations of 3-Chloro-2-(chloromethyl)-1-propene and 1,1-Dibromo-2,2-bis(chloromethyl)-cyclopropane: Intermediates in the Synthesis of [1.1.1]Propellane", J. Org. Chem., 1995, 60, 4666-4668.
Lynch, Kathleen M. and William P. Dailey, "[1.1.1]Propellane (Tricyclo[1.1.1.0$^{1,3}$]pentane)" Organic Syntheses, 1998, 75, 98-105 (online posting date: Apr. 28, 2003).
Plutschack, Matthew B., et al., "The Hitchhiker's Guide to Flow Chemistry", Chemical Reviews 2017 117(18), 11796-11893.
Porta, Riccardo, et al., "Flow Chemistry: Recent Developments in the Synthesis of Pharmaceutical Products", Org. Process Res. Dev. 2016, 20, 2-25.
Shtarev, Alexander B., et al., "Partially Bridge-Fluorinated Dimethyl Bicyclo[1.1.1]pentane-1,3-dicarboxylates: Preparation and NMR Spectra", J. Am. Chem. Soc. 2001, 123, 3484-3492.
Search Report and Written Opinion dated Dec. 10, 2018 in PCT Application No. PCT/US2018/049680 filed Sep. 6, 2018.
Extended European Search Report dated Mar. 6, 2021 in EP 18852929.1.
Klaus Semmler et al: "Tetracyclo[5.1.0.01 ,6.02,7]octane, a [1.1.1 ]poropellane derivative, and a new route to the parent hydrocarbon", Journal of the American Chemical Society, vol. 107, No. 22, Oct. 1, 1985 (Oct. 1, 1985), pp. 6410-6411.
Office Action issued in corresponding Indian Application No. 202017007752 dated Aug. 30, 2021.
Office Action received in Singapore Patent Application No. 11202001733V dated Nov. 18, 2021.
Office Action dated Mar. 9, 2022 in corresponding Israel Application No. 272875.
Office Action dated Mar. 17, 2022 in corresponding Australian Application No. 2018329815.
Office Action dated Mar. 28, 2022 in corresponding Russian Application No. 2020109427.

* cited by examiner

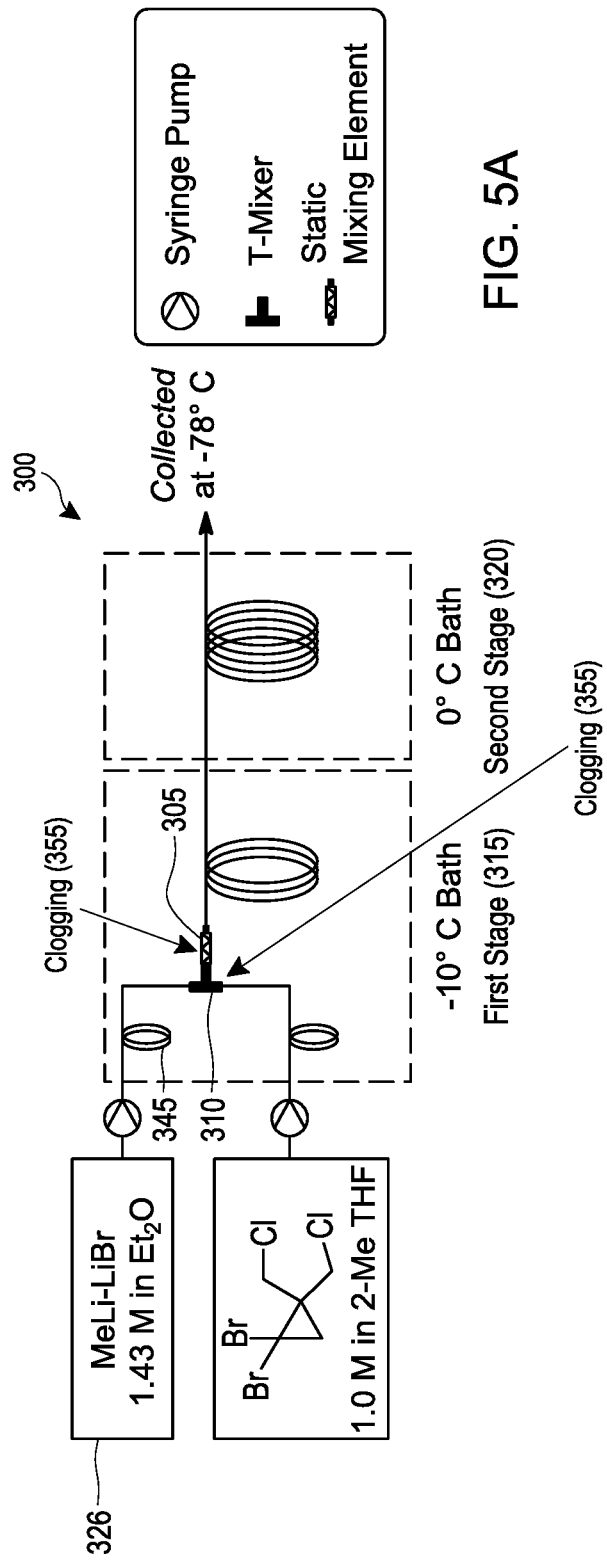
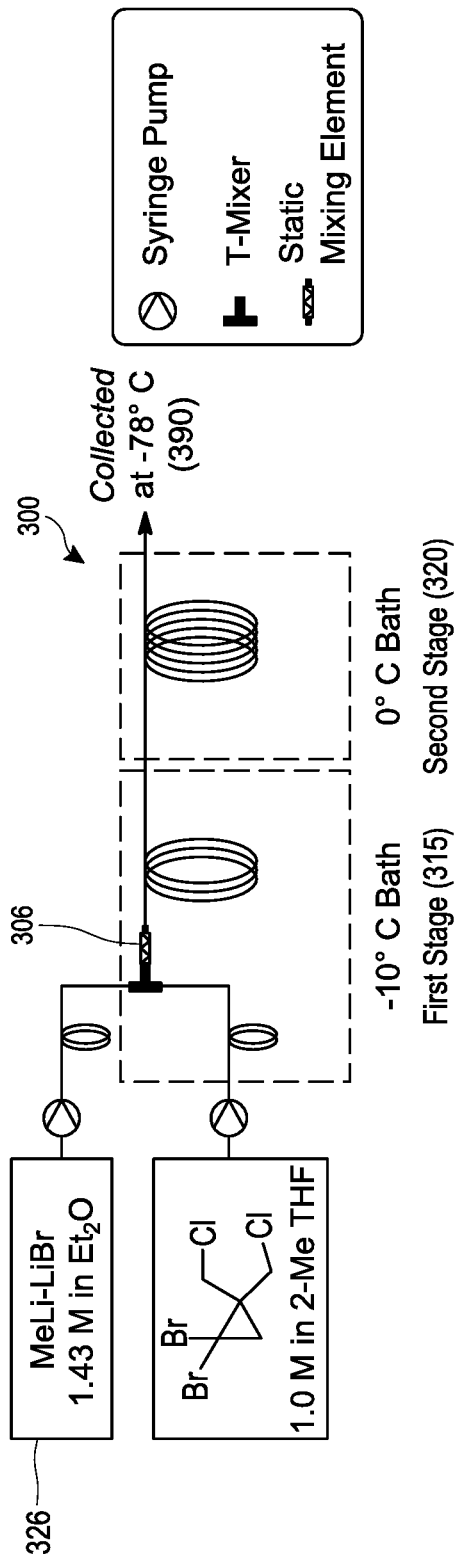
FIG. 5A
FIG. 5B

CONTINUOUS FLOW PROCESSES FOR MAKING BICYCLIC COMPOUNDS

INCORPORATION BY REFERENCE TO ANY PRIORITY APPLICATIONS

This application is a national stage filing of International Application No. PCT/US2018/049680, filed Sep. 6, 2018, which claims priority to U.S. Provisional Application Ser. No. 62/556,897, filed Sep. 11, 2017, both of which are hereby incorporated herein by reference in their entireties.

BACKGROUND

Field

This application relates to processes for making bicyclic compounds, and particularly for making [1.1.1]propellane and bicyclo[1.1.1]pentane and derivatives thereof using continuous flow reaction methods and conditions.

Description

Synthetic organic chemists have devised an enormous number of ways for making organic compounds. However, despite the wide scope and variety of known reaction pathways, most were developed, and are generally still practiced, under batch or semi-batch reaction conditions. For example, the traditional process (see K. R. Mondanaro and W. P. Dailey, Org. Synth. 75 (1998) p. 98) for making tricyclo[1.1.1.0$^{1,3}$]pentane (also known as [1.1.1]propellane) is a batch reaction of 1,1-dibromo-2,2-bis(chloromethyl)cyclopropane with methyllithium as follows:

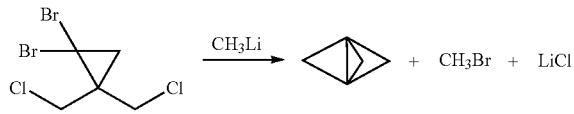

Continuous flow manufacturing of chemical compounds has generally been associated with high volume production of commodity materials. For example, continuous flow processes have been developed for making certain compounds, primarily in the realm of petrochemicals (e.g., gasoline) and consumer products (e.g., plastic packaging), having relatively simple chemical structures. More recently, synthetic organic chemists have begun to apply continuous flow reaction methods and conditions to the production of compounds having more complex chemical structures. These flow processes are in many cases safer, have higher throughput, and are more scalable compared to the original batch processes. For example, the use of flow chemistry for making pharmaceuticals has been recently reviewed. See R. Porta et al., "Flow Chemistry: Recent Developments in the Synthesis of Pharmaceutical Products", Org. Process Res. Dev. 2016, 20, 2-25, which is hereby incorporated herein by reference and particularly for the purpose of describing aspects of the current state of the art for flow chemistry.

However, in many cases the traditional chemical reaction pathways that were developed under batch or semi-batch reaction conditions have been found to behave differently under continuous flow reaction conditions. Although the reasons for the variations in behavior vary depending on the nature of the reaction, in many cases they have been attributed to large differences in heat transfer and mass transfer, particularly when the batch conditions are compared to those of a tubular reactor or microreactor in which the continuous flow reaction takes place under controlled conditions in a confined space. Therefore, there is generally little expectation that optimal continuous flow reaction conditions for a known reaction pathway can be successfully predicted on the basis of the corresponding batch reaction conditions. Accordingly, there remains a need for additional technical advances in the art of continuous flow manufacturing of complex chemical compounds.

SUMMARY

It has now been discovered that traditional batch reaction conditions for making highly strained bicyclic compounds such as [1.1.1]propellane and bicyclo[1.1.1]pentane (BCP) are not desirable for making such compounds under continuous flow reaction conditions. For example, as noted above the traditional batch process for making [1.1.1]propellane includes reacting 1,1-dibromo-2,2-bis(chloromethyl)cyclopropane with methyllithium using mixing, solvent, temperature and product isolation conditions exemplified by those described by K. R. Mondanaro and W. P. Dailey, Org. Synth. 75 (1998) p. 98. However, significant amounts of insoluble components are present under traditional batch solvent and temperature conditions, such as amounts of insoluble 1,1-dibromo-2,2-bis(chloromethyl)cyclopropane along with lithium chloride salt formed during the course of the reaction. Such insoluble components are considered tolerable for a batch process, or even desirable for enhancing yield and facilitating subsequent work up and isolation of [1.1.1]propellane. However, insoluble components tend to problematically clog the tubular reactors or microreactors typically used for continuous flow processes.

Continuous flow reaction methods and conditions have now been developed for making bicyclic compounds, and particularly for making [1.1.1]propellane and bicyclo[1.1.1]pentane and derivatives thereof. In various embodiments, the methods and conditions provide reducing clogging of the continuous flow reactor. For example, an embodiment provides a continuous flow process for making a bicyclic compound, comprising mixing 1,1-dibromo-2,2-bis(chloromethyl)cyclopropane with an organometallic reagent in a continuous flow reactor under reaction conditions selected to (a) react the 1,1-dibromo-2,2-bis(chloromethyl)cyclopropane with the organometallic reagent to produce [1.1.1]propellane and a salt; and (b) minimize clogging of the continuous flow reactor by the salt.

Another embodiment provides a continuous flow process for making 1,3-diacetylbicyclo[1.1.1]pentane, comprising mixing a [1.1.1]propellane composition with 2,3-butanedione in a continuous flow reactor under reaction conditions selected to react the [1.1.1]propellane with the 2,3-butanedione to produce 1,3-diacetylbicyclo[1.1.1]pentane. In an embodiment, the reaction conditions comprise exposing the [1.1.1.1]propellane and the 2,3-butanedione to a light source, such as an light emitting diode (LED). In literature examples, medium pressure mercury lamps have been exclusively used for the formation of 1,3-diacetylbicyclo [1.1.1]pentane. LED technology has several advantages over traditional mercury lamps including the ability to produce a single wavelength with high photon density, cost, and long lamp lifetime. In some embodiments, the [1.1.1]propellane composition is a substantially salt-free [1.1.1]propellane composition, e.g., as produced by a continuous flow process as described herein.

Another embodiment provides a continuous flow process for making a compound of Formula (I), comprising mixing [1.1.1]propellane with a magnesium amide reagent in a continuous flow reactor under reaction conditions selected to react the [1.1.1]propellane with the magnesium amide reagent to produce a compound of Formula (I). The structures of the magnesium amide reagent and the compound of Formula (I) are described below. In some embodiments, the [1.1.1]propellane is a composition produced by a continuous flow process as described herein. For example, in an embodiment the [1.1.1]propellane composition is a substantially salt-free [1.1.1]propellane composition, e.g., as produced by a continuous flow process as described herein.

Another embodiment provides a continuous flow process for making a compound of Formula (II), comprising mixing [1.1.1]propellane with a reagent of the formula $R^3$-$MX^1$ and a compound of the formula $R^4$—$X^2$ in a continuous flow reactor under reaction conditions selected to react the [1.1.1]propellane with the reagent of the formula $R^3$-$MX^1$ and the compound of the formula $R^4$—$X^2$ to produce a compound of Formula (II). The structures of the reagent of the formula $R^3$-$MX^1$, the compound of the formula $R^4$—$X^2$ and the compound of Formula (II) are described below. In an embodiment, the reaction conditions comprise the presence of a transition metal catalyst that is selected from the group consisting of a Pd catalyst and a Ni catalyst. In some embodiments, the [1.1.1]propellane is a composition produced by a continuous flow process as described herein. For example, in an embodiment the [1.1.1]propellane composition is a substantially salt-free [1.1.1]propellane composition, e.g., as produced by a continuous flow process as described herein.

Another embodiment provides a continuous flow process for making a compound of Formula (III), comprising mixing [1.1.1]propellane with a compound of the formula $R^5$—$X^3$ and carbon dioxide in a continuous flow reactor under reaction conditions selected to react the [1.1.1]propellane with the compound of the formula $R^5$—$X^3$ and the carbon dioxide to produce a compound of Formula (III). The structures of the compound of the formula $R^5$—$X^3$ and the compound of Formula (III) are described below. In some embodiments, the [1.1.1]propellane is a composition produced by a continuous flow process as described herein. For example, in an embodiment the [1.1.1]propellane composition is a substantially salt-free [1.1.1]propellane composition, e.g., as produced by a continuous flow process as described herein.

Another embodiment provides a continuous flow process for making a compound of Formula (IV), comprising mixing [1.1.1]propellane with a compound of the formula $R^5$—$X^3$ and a compound of the formula $X^4$—$CO_2R^6$ in a continuous flow reactor under reaction conditions selected to react the [1.1.1]propellane with the compound of the formula $R^5X^3$ and the compound of the formula $X^4$—$CO_2R^6$ to produce a compound of Formula (IV). The structures of the compound of the formula $R^5$—$X^3$, the compound of the formula $X^4$—$CO_2R^6$ and the compound of Formula (IV) are described below. In some embodiments, the [1.1.1]propellane is a composition produced by a continuous flow process as described herein. For example, in an embodiment the [1.1.1]propellane composition is a substantially salt-free [1.1.1]propellane composition, e.g., as produced by a continuous flow process as described herein.

Another embodiment provides a continuous flow process for making a compound of Formula (V), comprising mixing [1.1.1]propellane with a compound of the formula $R^7$—$X^5$ in a continuous flow reactor under reaction conditions selected to react the [1.1.1]propellane with the compound of the formula $R^7$—$X^5$ to produce a compound of Formula (V). The structures of the compound of the formula $R^7$—$X^5$ and the compound of Formula (V) are described below. In some embodiments, the [1.1.1]propellane is a composition produced by a continuous flow process as described herein. For example, in an embodiment the [1.1.1]propellane composition is a substantially salt-free [1.1.1]propellane composition, e.g., as produced by a continuous flow process as described herein.

Another embodiment provides a continuous flow process for making a compound of Formula (VI), comprising mixing [1.1.1]propellane with a compound of the formula $R^5X^3$ and water in a continuous flow reactor under reaction conditions selected to react the [1.1.1]propellane with the compound of the formula $R^5X^3$ and the water to produce a compound of Formula (VI). The structures of the compound of the formula $R^5X^3$ and the compound of Formula (VI) are described below. In some embodiments, the [1.1.1]propellane is a composition produced by a continuous flow process as described herein. For example, in an embodiment the [1.1.1]propellane composition is a substantially salt-free [1.1.1]propellane composition, e.g., as produced by a continuous flow process as described herein.

Another embodiment provides a continuous flow process for making 1,1-dibromo-2,2-bi s (chloromethyl)cyclopropane, comprising mixing 3-chloro-2-(chloromethyl)prop-1-ene with $CHBr_3$ in a continuous flow reactor under reaction conditions selected to produce the 1,1-dibromo-2,2-bis (chloromethyl)cyclopropane. In various embodiments, the reaction conditions comprise phase transfer conditions. For example, in an embodiment, the reaction conditions comprise mixing an organic solvent, an aqueous base and a phase transfer catalyst with the 3-chloro-2-(chloromethyl)prop-1-ene and the $CHBr_3$ in the continuous flow reactor under phase transfer reaction conditions.

These and other embodiments are described in greater detail below.

DRAWINGS

Figure 2:
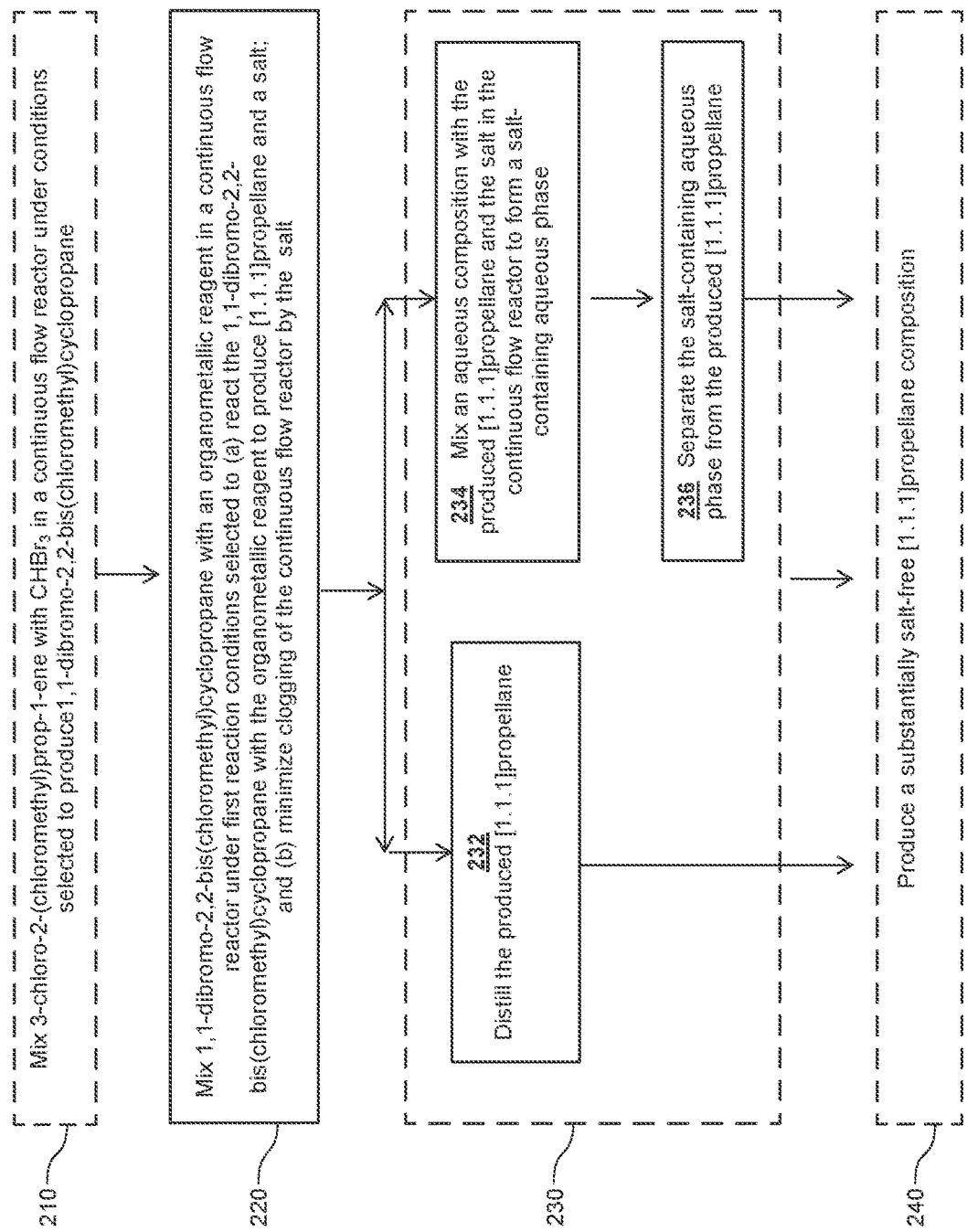

FIG. 2 schematically illustrates a flow diagram of an embodiment of a process for making [1.1.1]propellane under continuous flow reaction conditions.

Figure 3:
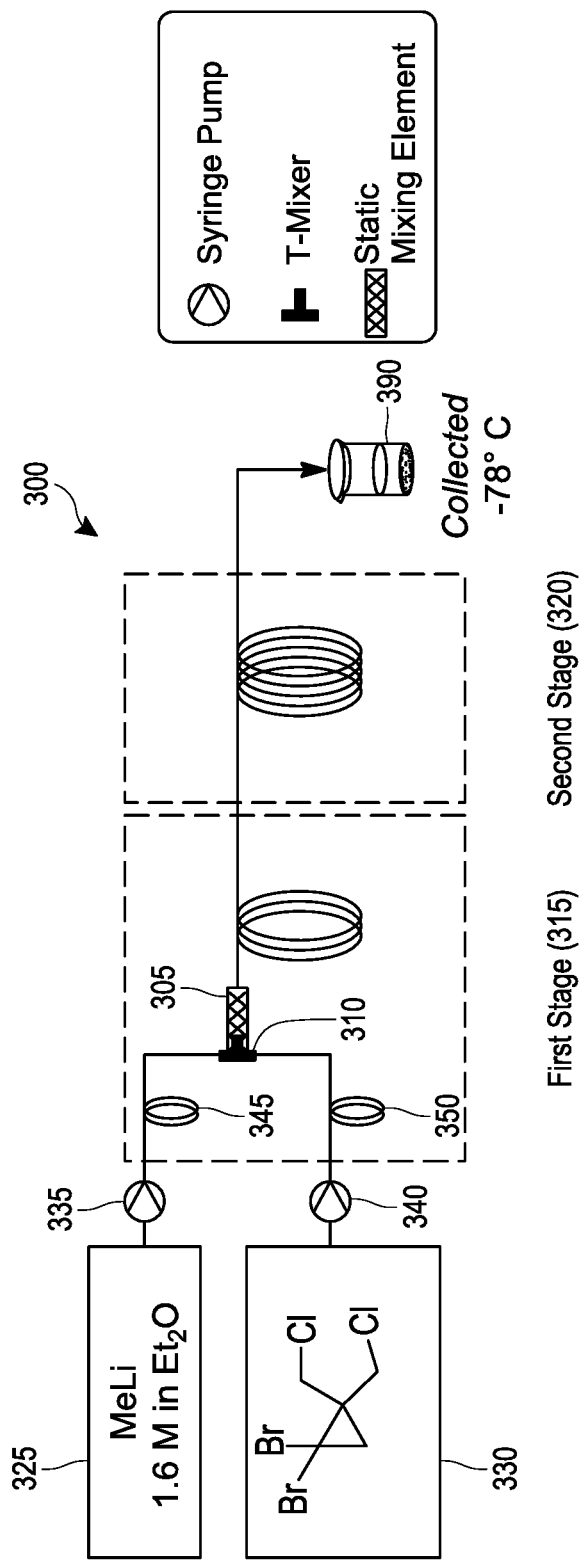

FIG. 3 schematically illustrates an embodiment of a process for making [1.1.1]propellane under continuous flow reaction conditions using a tubular reactor.

Figure 4:
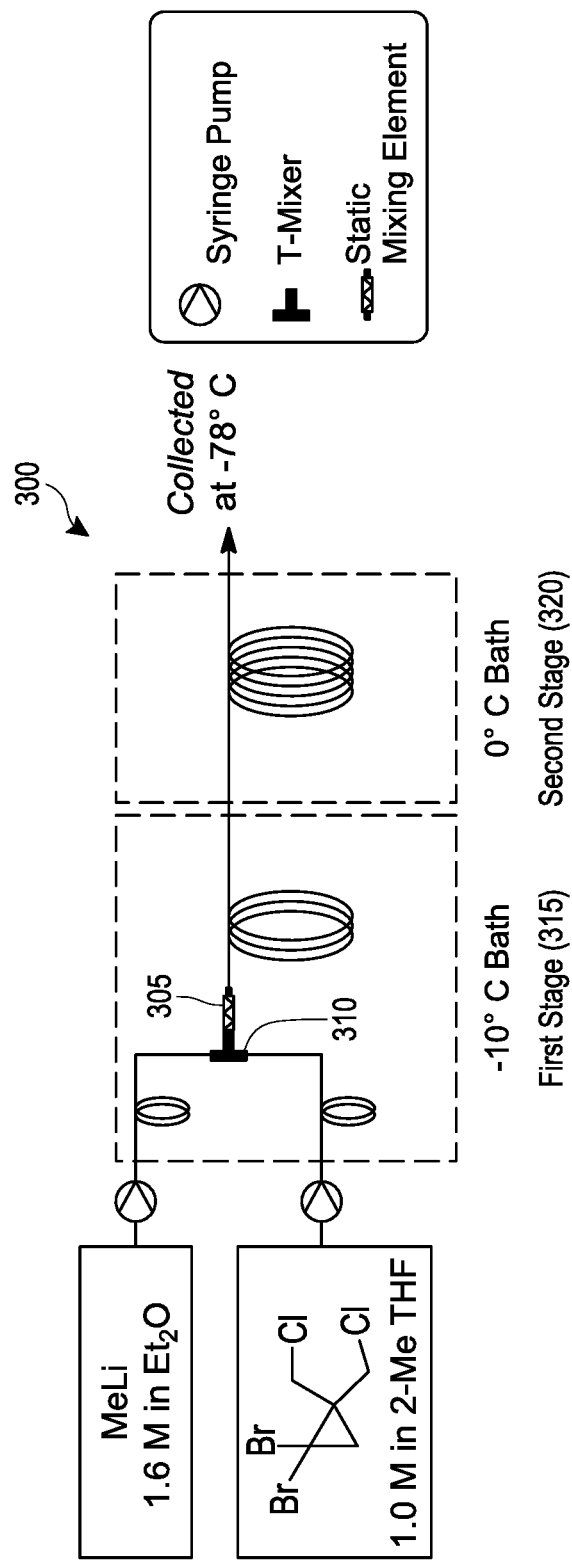

FIG. 4 schematically illustrates an embodiment of a process for making [1.1.1]propellane under continuous flow reaction conditions using a tubular reactor.

FIGS. 5A and 5B schematically illustrate embodiments of a process for making [1.1.1]propellane under continuous flow reaction conditions using a tubular reactor.

Figure 6:
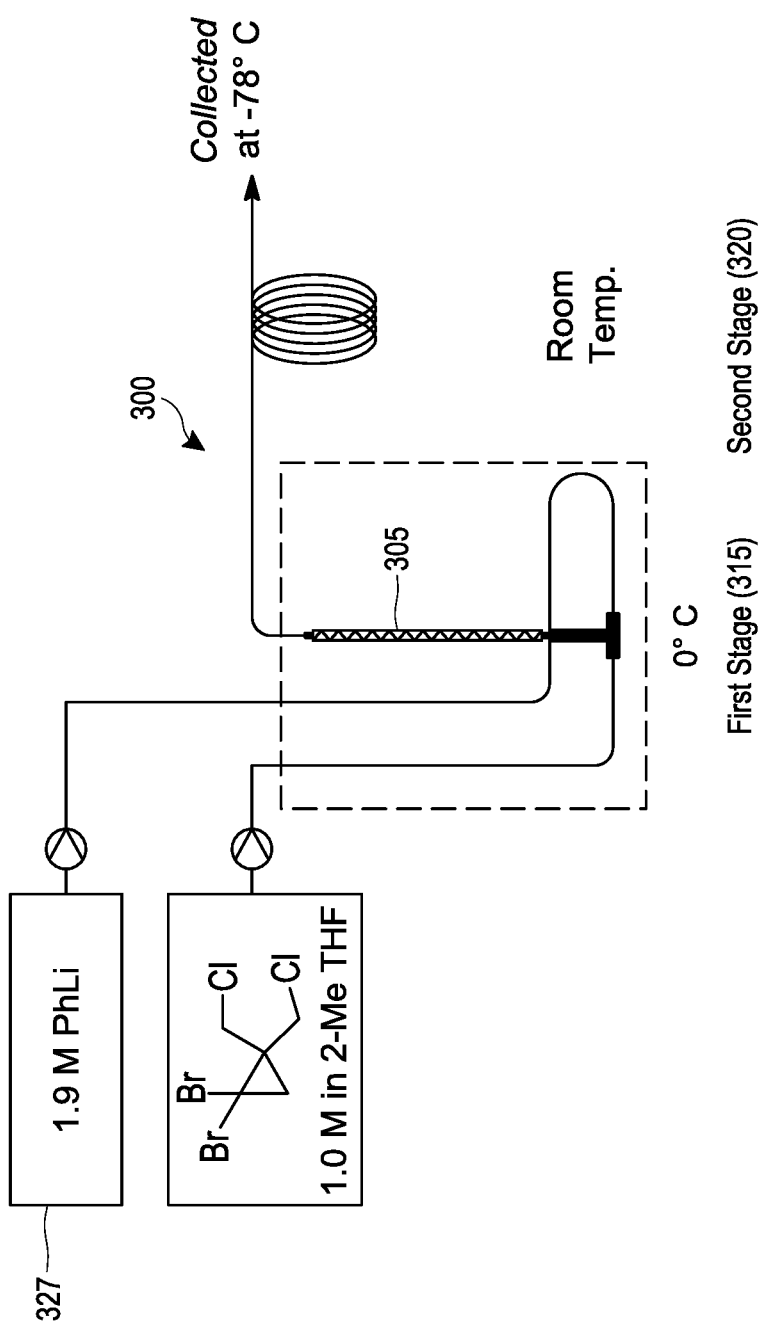

FIG. 6 schematically illustrates an embodiment of a process for making [1.1.1]propellane under continuous flow reaction conditions using a tubular reactor.

Figure 7:
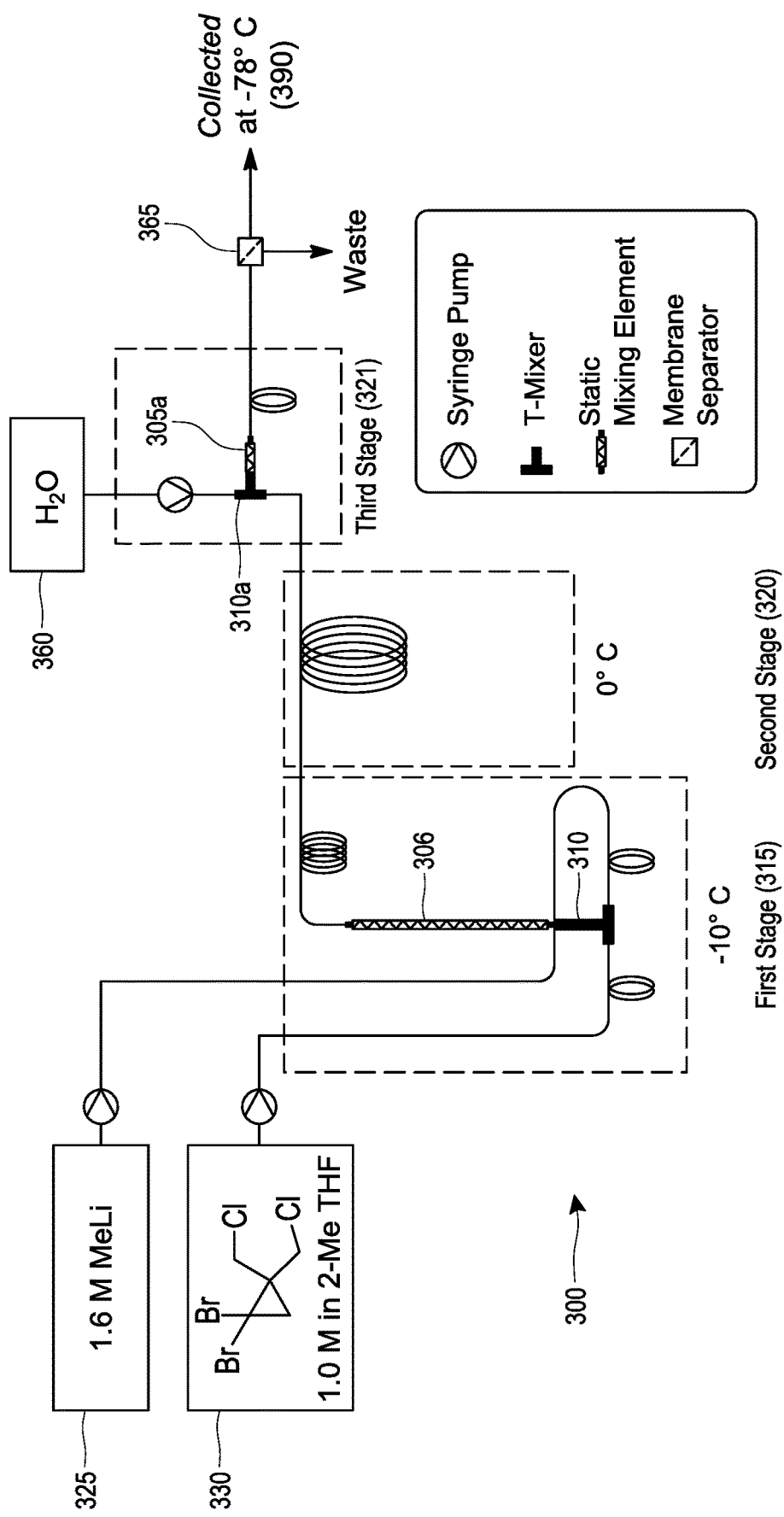

FIG. 7 schematically illustrates an embodiment of a process for making [1.1.1]propellane under continuous flow reaction conditions using a tubular reactor.

Figure 8:
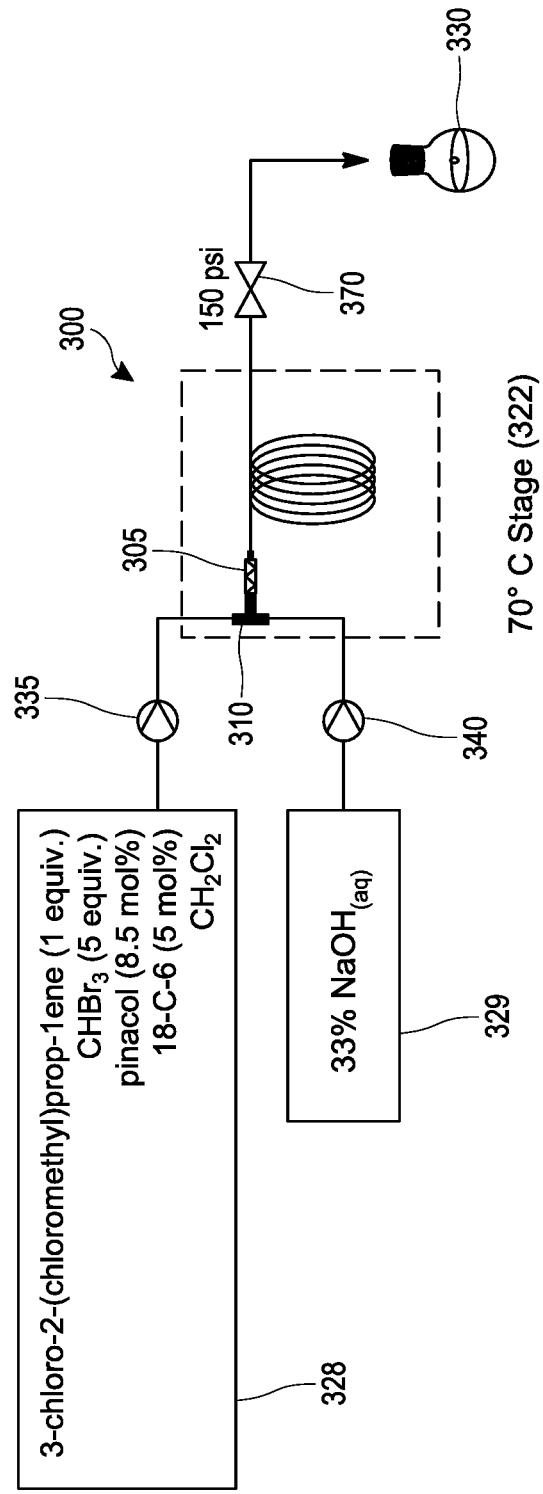

FIG. 8 schematically illustrates an embodiment of a process for making 1,1-dibromo-2,2-bis(chloromethyl)cyclopropane from 3-chloro-2-(chloromethyl)prop-1-ene under continuous flow reaction conditions using a tubular reactor.

Figure 9:
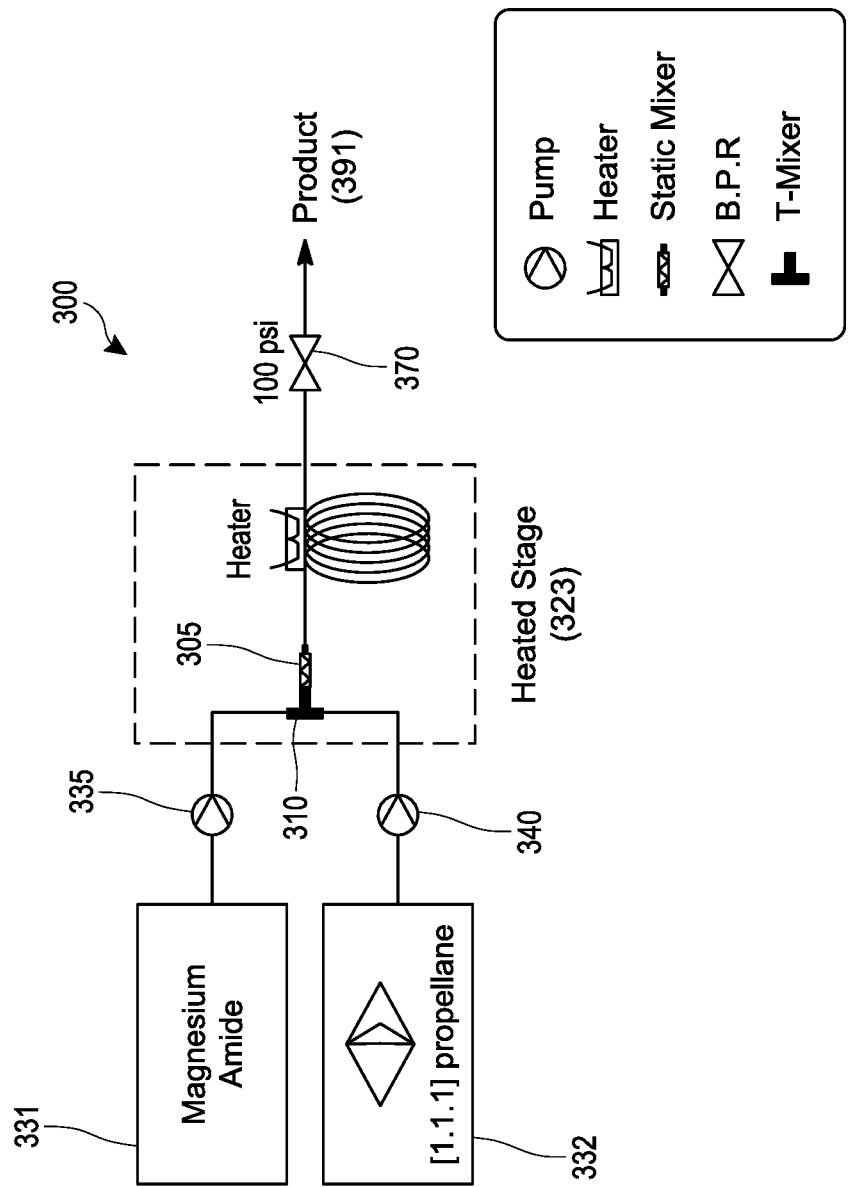

FIG. 9 schematically illustrates an embodiment of a process for making a bicyclo[1.1.1]pentyl amine (e.g., 1-(bicyclo[1.1.1]pentan-1-yl)indoline as described in Examples 30-38) under continuous flow reaction conditions using a tubular reactor.

Figure 10:
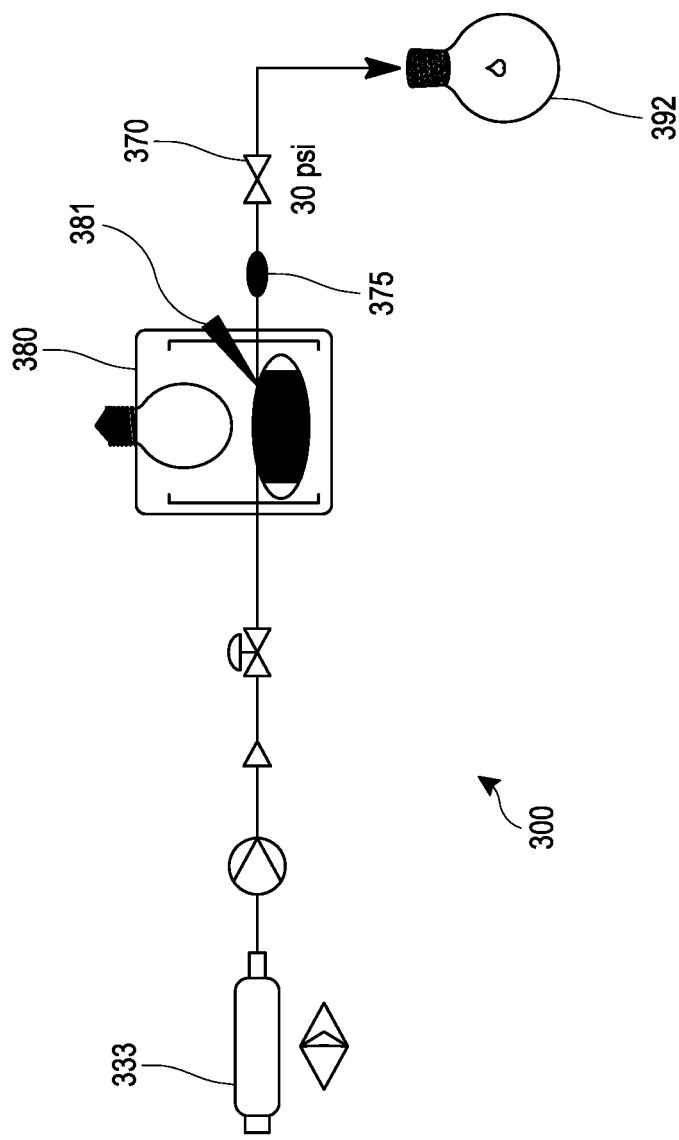

FIG. 10 schematically illustrates an embodiment of a process for making 1,3-diacetylbicyclo[1.1.1]pentane as described in Examples 42-47 under continuous flow reaction conditions using a tubular reactor.

Figure 11:
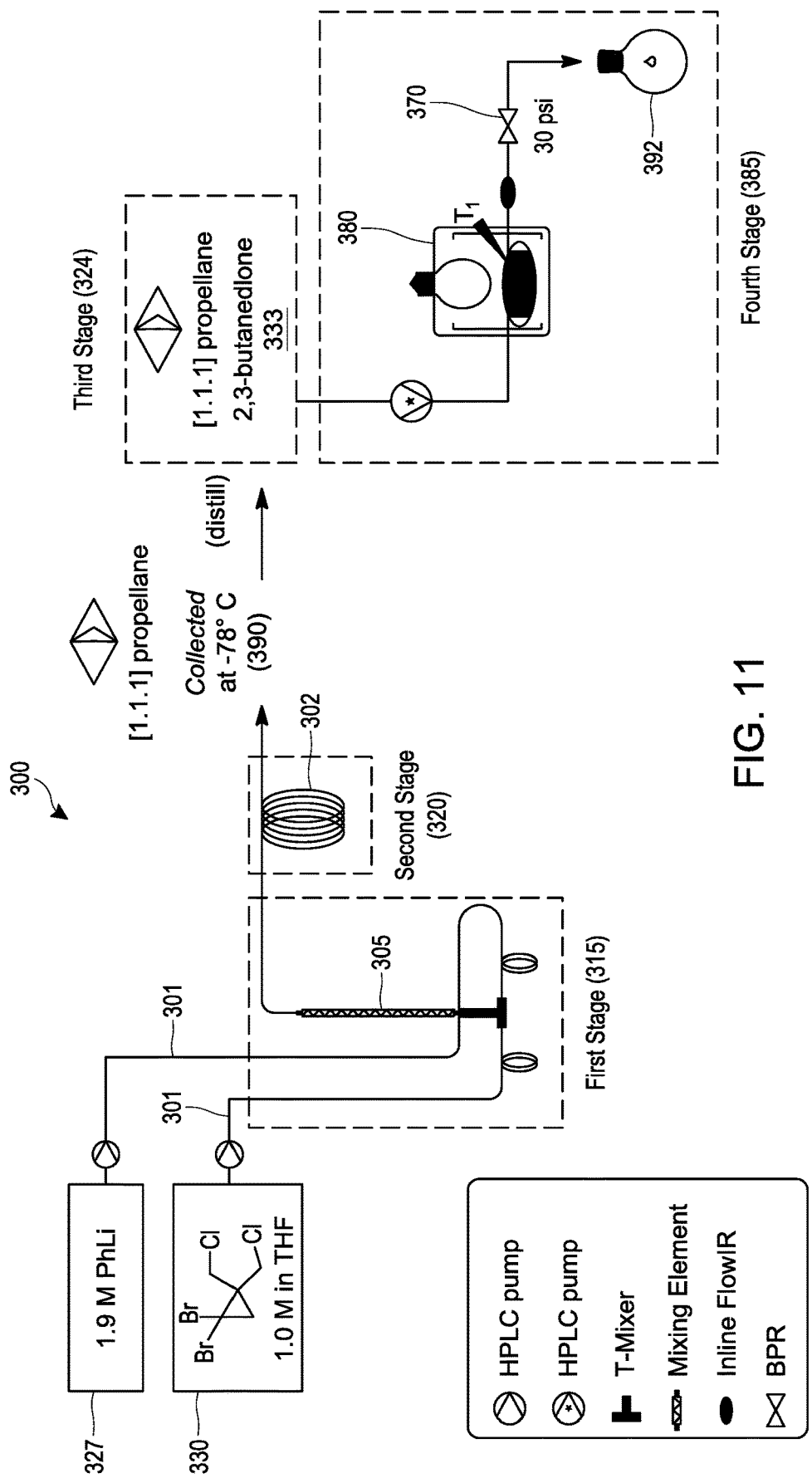

FIG. 11 schematically illustrates an embodiment of a process for making 1,3-diacetylbicyclo[1.1.1]pentane as described in Example 48 starting from 1,1-dibromo-2,2-bis(chloromethyl)cyclopropane under continuous flow reaction conditions using a multi-stage tubular reactor.

DETAILED DESCRIPTION

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, the term "continuous flow process" and similar terms are used to refer to a chemical process that utilizes flow chemistry and technology. Both single step and multiple step chemical reactions can be conducted using flow chemistry. Those skilled in the art recognize that flow chemistry involves the use of channels or tubing to conduct a chemical reaction (or series of chemical reactions) in a continuous stream rather than in separate batches using traditional vessels such as reaction flasks. Those skilled in the art are also aware of various kinds of continuous flow reactors in which flow chemistry may be conducted, such as tubular reactors (including spinning tube reactors), microreactors, spinning disk reactors, multi-cell flow reactors, oscillatory flow reactors, hex reactors and aspirator reactors. A continuous flow process can be scaled up or down, and therefore does not necessarily imply a particular continuous flow reactor size. In various embodiments the channels or tubing of the continuous flow reactor have a cross-sectional size (e.g., diameter for a tube having a circular cross-section) that is in the range of 1.5 mm to about 51 mm (e.g., from about 1/16 inch to about 2 inches). Thus, examples of cross-sectional size (e.g., diameter) for the channels or tubes of the include the following: about 1.5 mm or greater (e.g., about 1/16 inch or greater), about 3 mm or greater (e.g., about 1/8 inch or greater), about 6 mm or greater (e.g., about 1/4 inch or greater), about 9 mm or greater (e.g., about 3/8 inch or greater), about 13 mm or greater (e.g., about 1/2 inch or greater), about 25 mm or greater (e.g., about 1 inch or greater), about 51 mm or less (e.g., about 2 inches or less), about 25 mm or less (e.g., about 1 inch or less), about 22 mm or less (e.g., about 7/8 inch or less), about 19 mm or less (e.g., about 3/4 inch or less), about 16 mm or less (e.g., about 5/8 inch or less), about 13 mm or less (e.g., about 1/2 inch or less), about 9 mm or less (e.g., about 3/8 inch or less), or about 6 mm or less (e.g., about 1/4 inch or less). Those skilled in the art will understand that the aforementioned descriptions of channel or tubing sizes provide a description of ranges between suitable combinations, e.g., from about 3 mm (e.g., about 1/8 inch) to about 6 mm (e.g., about 1/4 inch). The terminology used herein with respect to continuous flow processes, flow chemistry and flow equipment is to be understood as having the ordinary meaning known to those skilled in the art. See M. B. Plutschack et al., "The Hitchhiker's Guide to Flow Chemistry" Chem. Rev. (June 2017), which is hereby incorporated by reference and particularly for the purpose of describing various continuous flow processes, flow chemistries, flow techniques and flow equipment. For any particular continuous flow process, scaling up or down can be accomplished by utilizing a continuous flow reactor having a larger or smaller tubing diameter, respectively. Scale up or down can also be achieved by increasing or decreasing the number of continuous flow reactors used to carry out the continuous flow. Reactor techniques and conditions, such as mixing, pressure, temperature, flow rate, reaction rate, reaction time and/or extent of reaction, can be controlled and/or monitored using known techniques and equipment such as vessels, tubing, pumps, valves, mixers, back pressure regulators (BPR), coolers, heaters, temperature sensors, temperature regulators, reaction monitors (such as in-line flow infrared (IR) monitor), photo reactors (e.g., equipped with UV source such as mercury lamp or 365 nm UV LED), membrane separators and computers. Those skilled in the art can control and monitor reactor conditions using routine experimentation informed by the detailed guidance and working examples provided herein. An embodiment provides a continuous flow reactor system that comprises one or more vessels, wherein the vessel(s) contains one or more chemical reagent(s) as described herein, such as [1.1.1]propellane, 1,1-dibromo-2,2-bis(chloromethyl)cyclopropane, and/or any of the other chemical reagents described in FIGS. 1C-D and the Examples below.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heterocyclyl, aryl(alkyl), cycloalkyl(alkyl), heteroaryl(alkyl), heterocyclyl(alkyl), hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, sulfenyl, sulfinyl, sulfonyl, haloalkyl, haloalkoxy, an amino, a mono-substituted amino group and a di-substituted amino group.

As used herein, "$C_a$ to $C_b$" (or $C_{a-b}$) in which "a" and "b" are integers refer to the number of carbon atoms in a group. The indicated group can contain from "a" to "b", inclusive, carbon atoms. Thus, for example, a "$C_1$ to $C_3$ alkyl" group (or $C_{1-3}$ alkyl group) refers to all alkyl groups (both linear and branched) having from 1 to 3 carbons, that is, $CH_3—$, $CH_3CH_2—$, $CH_3CH_2CH_2—$, and $(CH_3)_2CH—$. If no "a" and "b" are designated, the broadest range described in these definitions is to be assumed.

As used herein, the term "alkyl" refers to a fully saturated aliphatic hydrocarbon group. The alkyl moiety may be branched or straight chain. Examples of straight chain alkyl groups include methyl, ethyl, n-propyl, n-butyl, n-pentyl and n-hexyl. Examples of branched alkyl groups include iso-propyl, s-butyl, iso-butyl, and t-butyl. The alkyl group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, 4 carbon atoms, 5 carbon atoms or 6 carbon atoms).

As used herein, "alkenyl" refers to an alkyl group that contains in the straight or branched hydrocarbon chain one or more double bonds. Examples of alkenyl groups include allenyl, vinylmethyl, and ethenyl. An alkenyl group may be unsubstituted or substituted. In various embodiments, an alkenyl group contains 2 to 10 carbon atoms ($C_{2-10}$ alkenyl).

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. Cycloalkyl groups can contain 3 to 10 atoms in the ring(s), 3 to 8 atoms in the ring(s), 3 to 7 atoms in the ring(s), 3 to 6 atoms in the ring(s) or 3 to 5 atoms in the ring(s). A cycloalkyl group may be unsubstituted or substituted.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted. In various embodiments, a cycloalkenyl group contains 3 to 10 carbon atoms ($C_{3-10}$ alkenyl) or 5 to 10 carbon atoms ($C_{5-10}$ alkenyl).

As used herein, the term "fused" refers to a connectivity between two rings in which two adjacent atoms sharing at least one bond (saturated or unsaturated) are common to the rings. For example, in the following structure, rings A and B are fused

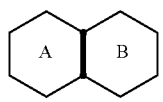

Examples of fused ring structures include, but are not limited to, decahydronaphthalene, 1H-indole, quinolone, chromane, bicyclo[2.1.0] pentane and 6,7,8,9-tetrahydro-5H-benzo[7] annulene.

As used herein, the term "bridged" refers to a connectivity wherein three or more atoms are shared between two rings. The following structures

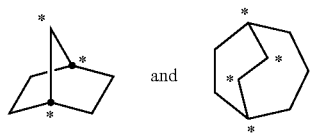 [SMILES: C1C[C@H]2CC[C@H]1C2 ; C1CC2CCC(C1)CC2]

are examples of "bridged" rings because the indicated atoms are shared between at least two rings. Examples of bridged ring structures include, but are not limited to, bicyclo[1.1.1] pentane, 2-oxabicyclo[1.1.1]pentane, 5-azabicyclo[2.1.1] hexane, 6-azabicyclo[3.1.1]heptane, adamantane and nor-bornane.

As used herein, the term "spiro" refers to a connectivity between two rings wherein the rings have only one atom in common. For example, in the structure

rings C and D are joined by a spiro connection. Examples of spiro connected ring structures include, but are not limited to, spiro[3.3]heptane, 2,6-diazaspiro[3.3]heptane, 2-oxa-6-azaspiro[3.3]heptane, spiro[4.5]decane and 2,6-dioxaspiro [3.3]heptane.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2, 3, 4 or 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring systems wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused, bridged or spiro fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidine, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of bridged heterocyclic compounds include, but are not limited to, 1,4-diazabicyclo[2.2.2]octane and 1,4-diazabicyclo[3.1.1]heptane. Examples of spiro-connected heterocyclic compounds include, but are not limited to, 2-azaspiro[3,3]heptane, 2,6-diazaspiro[3,3]heptane, and 2-oxa-6-azaspiro[3,3] heptane.

The term "halogen atom" or "halogen" as used herein, means any one of the radio-stable atoms of column 7 of the Periodic Table of the Elements, such as, fluorine, chlorine, bromine and iodine. The term "pseudohalide" as used herein, refers to the anions (or functional groups) of corresponding pseudohalogen groups. Examples of pseudohalides include cyanides, cyanates, isocyanates, thiocyanates isothiocyanates, selenocyanogens, tellurorhodanides, mesylates, triflates, tosylates and azides.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred','desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless the context indicates otherwise. Similarly, a group of items linked with the conjunction 'or' should not be read as requiring mutual exclusivity among that group, but rather should be read as 'and/or' unless the context indicates otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Figure 1A:
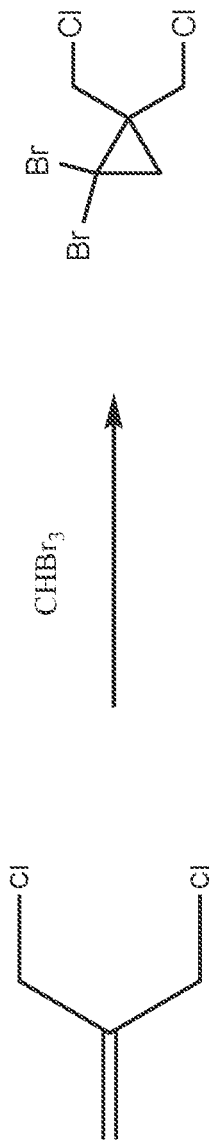
FIG. 1A illustrates a reaction scheme for making 1,1-dibromo-2,2-bis(chloromethyl)cyclopropane from 3-chloro-2-(chloromethyl)prop-1-ene under continuous flow reaction conditions.

FIGS. 1A-D illustrate reaction schemes that can be conducted under continuous flow reaction conditions. FIG. 1A illustrates a reaction scheme in a continuous flow process for making 1,1-dibromo-2,2-bis(chloromethyl)cyclopropane, comprising mixing 3-chloro-2-(chloromethyl)prop-1-ene with $CHBr_3$ in a continuous flow reactor under reaction conditions selected to react the 3-chloro-2-(chloromethyl)prop-1-ene with the $CHBr_3$ to produce 1,1-dibromo-2,2-bis(chloromethyl)cyclopropane.

Figure 1B:
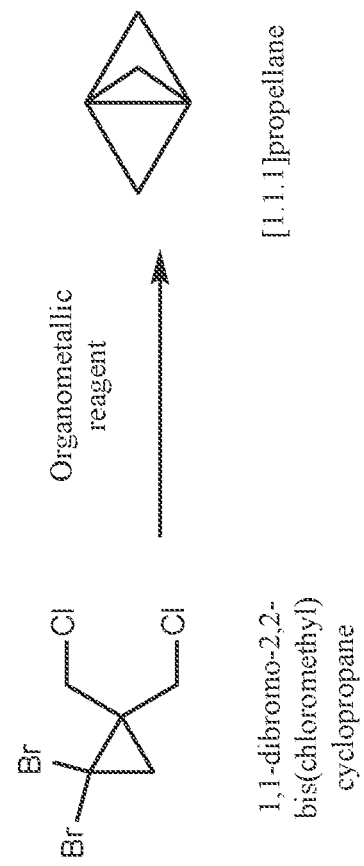
FIG. 1B illustrates a reaction scheme for making [1.1.1] propellane from 1,1-dibromo-2,2-bis(chloromethyl)cyclopropane under continuous flow reaction conditions.

FIG. 1B illustrates a reaction scheme in a continuous flow process for making a bicyclic compound, comprising mixing 1,1-dibromo-2,2-bis(chloromethyl)cyclopropane with an organometallic reagent in a continuous flow reactor under reaction conditions selected to (a) react the 1,1-dibromo-2,2-bis(chloromethyl)cyclopropane with the organometallic reagent to produce [1.1.1]propellane and a salt; and (b) minimize clogging of the continuous flow reactor by the salt.

Figure 1C:
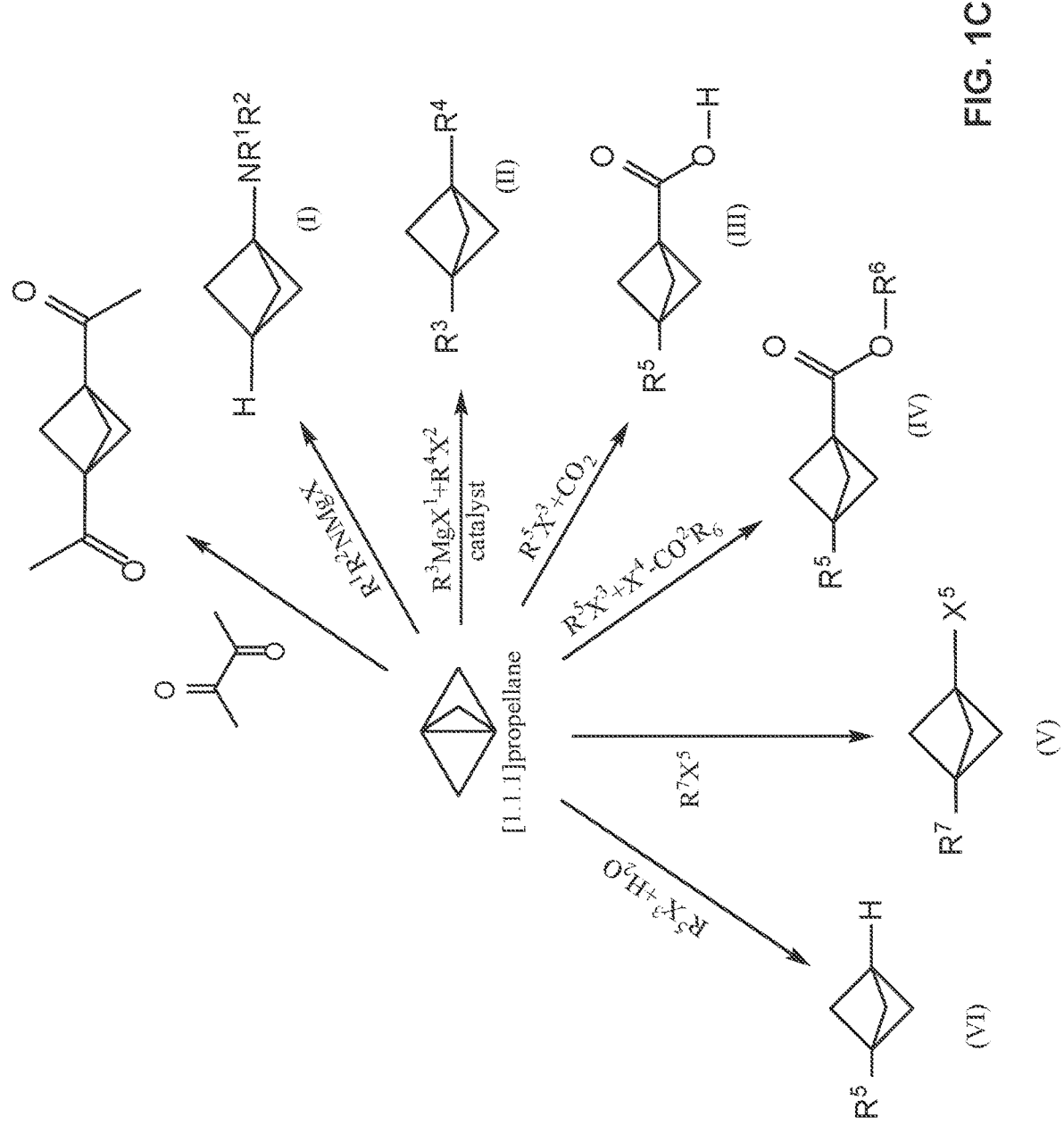
FIG. 1C illustrates reaction schemes for making 1,3-diacetylbicyclo[1.1.1]pentane (DABP) and compounds of Formulae (I), (II), (III), (IV), (V) and (VI) from [1.1.1] propellane under continuous flow reaction conditions.

FIG. 1C illustrates a variety of reaction schemes in continuous flow processes for making [1.1.1]propellane derivatives. In the illustrated embodiment, the [1.1.1]propellane derivatives are 1,3-diacetylbicyclo[1.1.1]pentane (DABP) and compounds of Formulae (I), (II), (III), (IV), (V) and (VI).

Figure 1D:
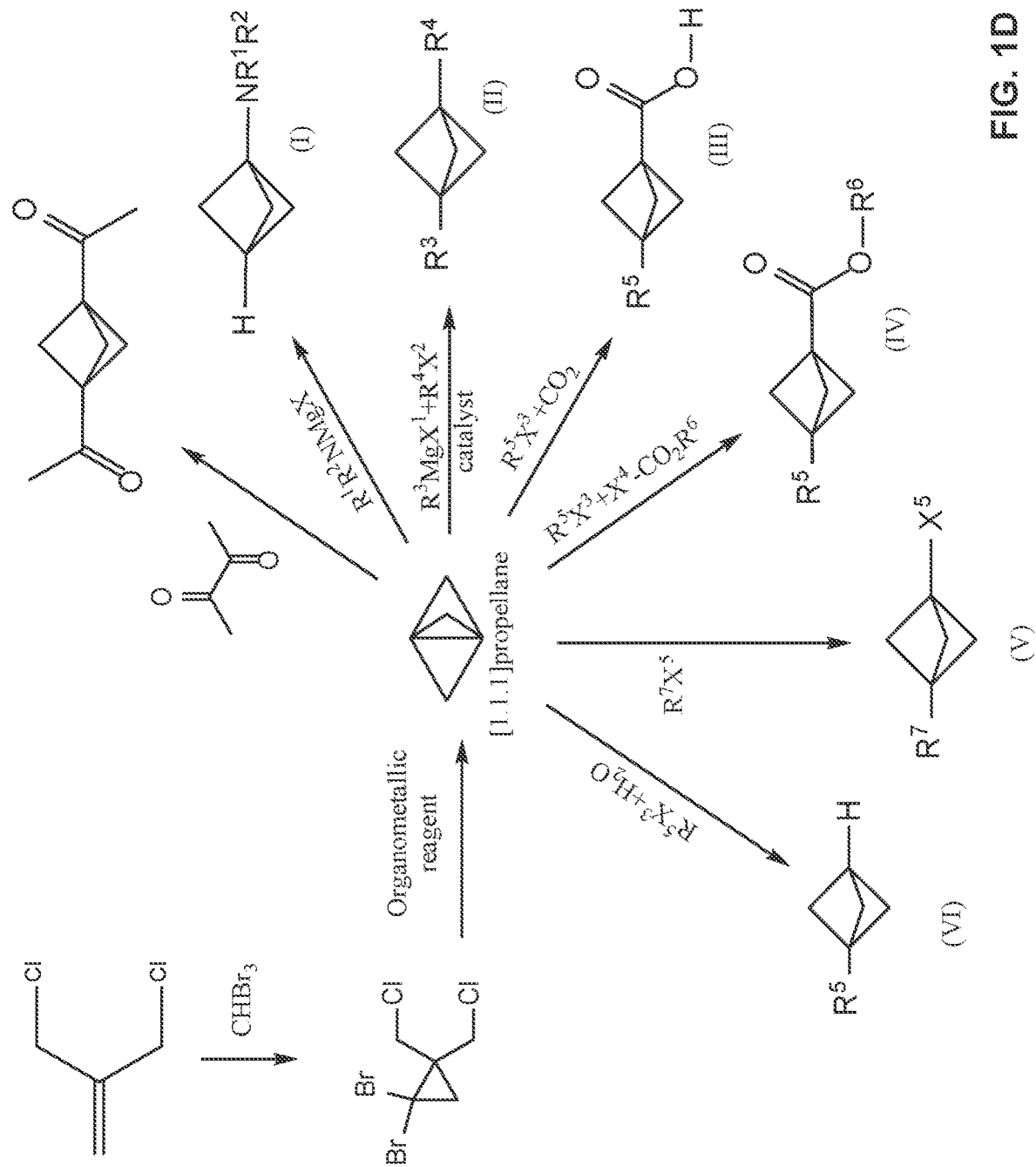
FIG. 1D illustrates multi-step reaction schemes for making 1,1-dibromo-2,2-bis(chloromethyl)cyclopropane, [1.1.1]propellane, 1,3-diacetylbicyclo[1.1.1]pentane (DABP), and compounds of Formulae (I), (II), (III), (IV), (V) and (VI) under continuous flow reaction conditions.

Continuous flow processes for carrying out each of the reaction schemes illustrated in FIGS. 1A-C are described in greater detail elsewhere herein. In some embodiments those descriptions include conducting the reactions sequentially, e.g., as illustrated in FIG. 1D. However, those skilled in the art will appreciate that each of the continuous flow processes for carrying out each of the reaction schemes illustrated in FIGS. 1A-C can be practiced individually. Those skilled in the art will also appreciate that each of the continuous flow processes for carrying out each of the reaction schemes illustrated in FIGS. 1A-C can be practiced in any suitable sequential or non-sequential combination. For example, in various embodiments the illustrated reaction schemes can be carried out in sequential or non-sequential combinations as summarized in Table 1. Suitable sequential or non-sequential combinations can be conducted with or without isolation of the product of the prior step.

TABLE 1

| No. | 1A | 1B | 1C (DABP) | 1C (I) | 1C (II) | 1C (III) | 1C (IV) | 1C (V) | 1C (VI) |
|---|---|---|---|---|---|---|---|---|---|
| | | | Reaction Sequence (Figure No.) | | | | | | |
| 1 | X | X | | | | | | | |
| 2 | X | | X | | | | | | |
| 3 | X | | | X | | | | | |
| 4 | X | | | | X | | | | |
| 5 | X | | | | | X | | | |
| 6 | X | | | | | | X | | |
| 7 | X | | | | | | | X | |
| 8 | X | | | | | | | | X |
| 9 | | X | X | | | | | | |
| 10 | | X | | X | | | | | |
| 11 | | X | | | X | | | | |
| 12 | | X | | | | X | | | |
| 13 | | X | | | | | X | | |
| 14 | | X | | | | | | X | |
| 15 | | X | | | | | | | X |
| 16 | X | X | X | | | | | | |
| 17 | X | X | | X | | | | | |
| 18 | X | X | | | X | | | | |
| 19 | X | X | | | | X | | | |
| 20 | X | X | | | | | X | | |
| 21 | X | X | | | | | | X | |
| 22 | X | X | | | | | | | X |

Continuous Flow Process for Making [1.1.1]Propellane

Various embodiments provide continuous flow processes for making bicyclic compounds, and particularly for making [1.1.1]propellane and derivatives thereof. For example, in various embodiments a continuous flow process utilizing flow chemistry is used to react 1,1-dibromo-2,2-bis(chloromethyl)cyclopropane with an organometallic reagent in a continuous flow reactor to make [1.1.1]propellane as illustrated in FIGS. 1B, 1D and 2. As noted above, it has now been found that the traditional batch conditions for conducting this reaction result in significant amounts of insoluble components (such as insoluble 1,1-dibromo-2,2-bis(chloromethyl)cyclopropane, LiCl salt and/or LiBr salt) that tend to problematically clog the tubing or channels of continuous flow reactors.

In various embodiments, reaction conditions have been identified that produce acceptable yields of [1.1.1]propellane while minimizing clogging of the continuous flow reactor by the salt(s). For example, whereas the traditional reaction conditions include mixing the 1,1-dibromo-2,2-bis (chloromethyl)cyclopropane with methyllithium in pentane in a first stage at −78° C. to −50° C., following by stirring in a second stage at −0° C., it has now been found that the reaction can be conducted in a continuous flow process using reaction conditions that include significantly higher temperatures.

For example, in an embodiment, 1,1-dibromo-2,2-bis (chloromethyl)cyclopropane is mixed with an organometallic reagent in a continuous flow reactor as illustrated in step 220 of FIG. 2. The reaction conditions are selected at step 220 to (a) react the 1,1-dibromo-2,2-bis(chloromethyl)cyclopropane with the organometallic reagent to produce [1.1.1]propellane and a salt; and (b) minimize clogging of the continuous flow reactor by the salt.

The 1,1-dibromo-2,2-bis(chloromethyl)cyclopropane utilized in step 220 may be synthesized or obtained commercially. Optionally, the synthesis of the 1,1-dibromo-2,2-bis (chloromethyl)cyclopropane may be conducted in the continuous flow reactor in an optional prior step 210 as illustrated in FIG. 2 by carrying out the reaction illustrated by the reaction scheme in FIG. 1A in a continuous flow reactor. Thus, in an embodiment the process of step 210 comprises mixing 3-chloro-2-(chloromethyl)prop-1-ene with $CHBr_3$ in the continuous flow reactor under reaction conditions selected to produce the 1,1-dibromo-2,2-bis (chloromethyl)cyclopropane. In an embodiment, the reaction conditions include mixing an aqueous base (e.g., aqueous NaOH and/or aqueous KOH). In another embodiment, the reaction conditions include the presence of an organic solvent, such as $CH_2C_{12}$ or $CHCl_3$. In another embodiment, the reaction conditions include phase transfer conditions comprising a catalytically effective amount (e.g., from about 1 mol % to about 10 mol %, based on 3-chloro-2-(chloromethyl)prop-1-ene) of a phase transfer catalyst, such as pinacol and/or a crown ether such as 18-crown-6 and/or benzo-18-crown-6. In another embodiment, the reaction conditions include a reaction temperature in the range of about 0° C. to about 80° C. In another embodiment, the reaction conditions include mixing the 3-chloro-2-(chloromethyl)prop-1-ene, $CHBr_3$ and aqueous base in a continuous flow reactor equipped with a static mixer that is effective to enhance the reaction rate (e.g., by facilitating phase transfer conditions). As discussed elsewhere herein (see, e.g., Table 1), the process of mixing 3-chloro-2-(chloromethyl)prop-1-ene with $CHBr_3$ in the continuous flow reactor under conditions selected to produce the 1,1-dibromo-2,2-bis(chloromethyl) cyclopropane can be carried out separately as a standalone process, sequentially with another process step (e.g., as illustrated by steps 210 and 220 in FIG. 2), or non-sequentially with another process step (e.g., as summarized in Table 1).

The reaction conditions selected at step 220 may comprise a reaction temperature in the range of about −50° C. to about 0° C.; about −50° C. to about −10° C.; about −40° C. to about 0° C.; about −40° C. to about −10° C.; about −30° C. to about 0° C. or about −30° C. to about −10° C. Examples of other reaction conditions that can be used in combination with such reaction temperatures are described elsewhere herein and/or are exemplified in the Examples below.

In various embodiments, the reaction conditions for mixing the 1,1-dibromo-2,2-bis(chloromethyl)cyclopropane with the organometallic reagent in a continuous flow reactor at step 220 can include a single stage or multiple stages (e.g., 2, 3, 4 or more stages) in which one or more reaction conditions (such as the reaction temperatures described above) can be varied throughout the course of the reaction, on a stepwise or continuous basis. For example, in a first stage the reaction conditions can include a first reaction temperature in any of the temperature ranges described above. In a second stage, the first reaction temperature can be changed to a second reaction temperature in the range of about −20° C. to about 20° C.; about −20° C. to about 10° C.; about −20° C. to about 0° C.; about −20° C. to about −10° C.; about −10° C. to about 25° C.; about −10° C. to about 20° C.; about −10° C. to about 10° C.; or about −10° C. to about 0° C. Examples of other reaction conditions that can be used in combination with single or multiple reaction stages are described elsewhere herein and/or are exemplified in the Examples below. Flow reactor conditions (such as flow rate) that affect the rate or product of the reaction are considered reaction conditions. Thus, in addition to temperature stages, examples of other reaction stages include flow rate stages, mixing stage(s), irradiation stages, dilution stage(s), separation stage(s) (e.g., membrane separation, distillation), purification stage(s) (e.g., filtering, washing) and product isolation stage(s). As explained in greater detail elsewhere herein, the additional stage(s) may comprise further reacting the produced [1.1.1]propellane with other reagents, with or without an intermediate isolation step, to produce [1.1.1]propellane derivatives, e.g., as illustrated in FIGS. 1C and 1D.

As noted above, the traditional batch reaction conditions for producing [1.1.1]propellane include mixing 1,1-dibromo-2,2-bis(chloromethyl)cyclopropane in pentane with methyllithium. Methyllithium is often available commercially as a solution in diethyl ether and thus traditional reaction solvent mixtures contain both pentane and diethyl ether. The addition of methyl lithium to 1,1-dibromo-2,2-bis(chloromethyl)cyclopropane is typically performed at temperatures ranging from −78 to −50° C. While not an issue in small batch reactions, cooling kilogram scale reactions to low temperatures leads to increased costs and scalability issues. It has now been found that when the reaction is conducted in a continuous flow process, the reaction temperatures can be increased to −20° C. and higher. In addition, it has now been found that additional organometallic reagents that form precipitation products in batch syntheses of [1.1.1]propellane can be used in a continuous flow process. For example in an embodiment, the organometallic reagent selected in step 220 is n-butyllithium, methyllithium, methyllithium lithium bromide complex, or phenyllithium.

It has now been found that the reaction of 1,1-dibromo-2,2-bis(chloromethyl)cyclopropane with an organometallic reagent can be conducted in a continuous flow process using reaction conditions selected at step 220 that include solvents and solvent mixtures other than mixtures of pentane and diethyl ether. In an embodiment, the reaction conditions comprise mixing a solvent with the 1,1-dibromo-2,2-bis(chloromethyl)cyclopropane and the organometallic reagent in the continuous flow reactor, wherein the solvent is selected from the group consisting of diethylether, diethoxymethane, dibutylether, methyl tert-butyl ether, tetrahydrofuran, 2-methyltetrahydrofuran and mixtures thereof. The solvent(s) may be added to the continuous flow reactor separately, or may be added along with the 1,1-dibromo-2,2-bis(chloromethyl)cyclopropane and/or the organometallic reagent. For example, in an embodiment in which a solution of phenyllithium in dibutylether is used as the organometallic reagent, the reaction conditions will include the presence of the dibutylether. Likewise, in an embodiment in which a solution of methyllithium in diethoxymethane is used as the organometallic reagent, the reaction conditions will include the presence of the diethoxymethane. Similarly, the reaction conditions may include a solvent introduced into the continuous flow reactor with 1,1-dibromo-2,2-bis(chloromethyl)cyclopropane, such as tetrahydrofuran, 2-methyltetrahydrofuran or a mixture thereof. In various embodiments, the reaction conditions include a solvent selected from diethyl ether; a mixture of diethyl ether and tetrahydrofuran; a mixture of diethyl ether and 2-methyltetrahydrofuran; a mixture of dibutyl ether and tetrahydrofuran; or a mixture of dibutyl ether and 2-methyltetrahydrofuran. Examples of other reaction conditions that can be used in combination with the solvent conditions described herein are described elsewhere herein and/or are exemplified in the Examples below.

In addition to the mixing that occurs at step 220 when the 1,1-dibromo-2,2-bis(chloromethyl)cyclopropane contacts the organometallic reagent within the continuous flow reactor, it has been found that additional mixing within the reactor minimizes clogging by the salt(s) while producing acceptable yields of [1.1.1]propellane. Such additional internal mixing can be supplied in various ways. For example, in various embodiments, the continuous flow reactor is equipped with one or more inline static mixers. Those skilled in the art understand that static mixers provide inline mixing without moving parts by including mixing elements within the flow path that divide and recombine the components as they flow through the mixer. A wide variety of inline static mixers are commercially available with various lengths, diameters and internal configurations. Commercial sources of inline static mixers include, for example, Sta-MixCo LLC (New York).

In various embodiments, the continuous flow reactor comprises a static mixer and the mixing of the 1,1-dibromo-2,2-bis(chloromethyl)cyclopropane with the organometallic reagent is conducted with the static mixer at a mixing rate that is effective to minimize clogging of the continuous flow reactor by the salt. Those skilled in the art appreciate that the mixing rate within the continuous flow reactor can be controlled by selecting an inline static mixer of the appropriate size and internal configuration for the continuous flow reactor and the selected reaction conditions (e.g., flow rate, temperature and concentration of reactants). Selection of the appropriate static mixer can be achieved by routine experimentation informed by the guidance provided herein. In an embodiment, the inline static mixer has a diameter that is about the same as, or larger, than that of the reactor tubing to which it is attached, e.g., from about the same diameter to about twice the diameter of the reactor tubing.

In various embodiments, after one or more stages during which the 1,1-dibromo-2,2-bis(chloromethyl)cyclopropane is reacted with the organometallic reagent in the continuous flow reactor to produce [1.1.1]propellane and a salt as described elsewhere herein, the continuous flow process may include an optional post-reaction stage 230. For example, in an embodiment, the post-reaction stage 230 is an optional purification stage as illustrated in FIG. 2. In an embodiment of the purification stage 230, the produced [1.1.1]propellane and the salt are separated, e.g., by distillation 232 as illustrated in FIG. 2, to produce a substantially salt-free [1.1.1]propellane composition 240.

Another embodiment of the post-reaction stage 230 (illustrated as the purification stage 230 in FIG. 2) comprises mixing an aqueous composition with the produced [1.1.1]propellane and the salt in the continuous flow reactor to form a salt-containing aqueous phase at step 234. The pH of the aqueous composition can be adjusted as desired by including appropriate amounts of acid, base or buffer. Since the salts produced during the course of the reaction generally have much greater solubility in water than in the organic phase (depending on the choice of solvent), separating the salt-containing aqueous phase from the produced [1.1.1]propellane provides a way to at least partially purify the [1.1.1] propellane, which can then be isolated or further reacted in subsequent stages within the continuous flow reactor or by extending it, e.g., as described elsewhere herein. Thus, in various embodiments, after the aqueous composition is mixed with the produced [1.1.1]propellane and the salt in the continuous flow reactor to form a salt-containing aqueous phase, the process further comprises separating the salt-containing aqueous phase from the produced [1.1.1]propellane at step 236 to thereby produce a substantially salt-free [1.1.1]propellane composition 240. Separating can be carried out in various ways, e.g., by using membrane separation as illustrated in Example 28 and FIG. 7. Although the distillation step 232 is depicted in FIG. 2 as being an alternative to purifications steps 234 and 236, those skilled in the art will appreciate that the order of the steps can be changed and/or the steps can be combined. For example, in an embodiment (not illustrated), distillation 232 can be conducted before or after each of steps 234 and 236, and/or after step 240.

Continuous Flow Process for Making [1.1.1]Propellane Derivatives

Various embodiments provide a continuous flow process for making a [1.1.1]propellane derivative that comprises mixing a [1.1.1]propellane composition with a selected reagent in a continuous flow reactor under reaction conditions selected to react the produced [1.1.1]propellane with the selected reagent to produce the desired [1.1.1]propellane derivative. In various embodiments the reaction conditions are selected to minimize clogging of the continuous flow reactor by insoluble components formed during the reaction. The [1.1.1]propellane composition may be produced in various ways, including by traditional batch methods or by the continuous flow methods described herein. In various embodiments the [1.1.1]propellane composition used in this reaction is one that has been at least partially purified, such as a substantially salt-free [1.1.1]propellane composition as described elsewhere herein. Those skilled in the art will appreciate that the [1.1.1]propellane composition can be prepared in a continuous flow process as described herein and then isolated prior to being used to make the [1.1.1] propellane derivative. However, such isolation is not necessary. In an embodiment, the [1.1.1]propellane composition produced as described herein can be used directly, without isolation, in the continuous flow process for making the [1.1.1]propellane derivative, e.g., in effect by adding additional stages to the continuous flow process illustrated in FIG. 2. Examples of [1.1.1]propellane derivatives that may be prepared are illustrated in FIGS. 1C and 1D and are described in greater detail below.

An embodiment provides a continuous flow process for making 1,3-diacetylbicyclo[1.1.1]pentane (DABP), comprising mixing a [1.1.1]propellane composition produced as described herein (such as a substantially salt-free [1.1.1]propellane composition) with 2,3-butanedione in a continuous flow reactor under reaction conditions selected to react the produced [1.1.1]propellane with the 2,3-butanedione to produce 1,3-diacetylbicyclo[1.1.1]pentane. The [1.1.1]propellane composition may be produced in various ways, including by traditional batch methods or by the continuous flow methods described herein, and thus may be a substantially salt-free [1.1.1]propellane composition as described herein. In an embodiment, the reaction conditions comprise exposing the produced [1.1.1]propellane and the 2,3-butanedione to a light source. In an embodiment, the light source is an ultraviolet light source, e.g., a source of radiation in the range of about 350 nm to about 380 nm. Various light sources can be used, such as a 400 W mercury lamp. In an embodiment, the light source comprises a light emitting diode. The continuous flow reactor preferably comprises tubing that is at least partially transparent to ultraviolet radiation, such as quartz tubing. In such an embodiment, is not necessary that the entire continuous flow reactor be constructed of such transparent tubing, so long as it contains a sufficiently lengthy section that is configured to contain the mixture of produced [1.1.1]propellane and the 2,3-butanedione for exposure to the light source.

An embodiment provides a continuous flow process for making a compound of Formula (I):

(I)

In Formula (I), $R^1$ and $R^2$ are each individually selected from the group consisting of hydrogen, an optionally substituted $C_{1-10}$ alkyl, an optionally substituted $C_{3-10}$ monocyclic cycloalkyl, an optionally substituted $C_{6-10}$ aryl, an optionally substituted ($C_{6-10}$ aryl)alkyl, an optionally substituted $C_{5-10}$ heteroaryl, an optionally substituted ($C_{5-10}$ heteroaryl)alkyl, phenyl and benzyl; or $R^1$, $R^2$ and the nitrogen to which they are attached together form an optionally substituted heterocyclyl. In various embodiments, the process for making the compound of Formula (I) comprises mixing a [1.1.1]propellane composition with a magnesium amide reagent in a continuous flow reactor under reaction conditions selected to react the [1.1.1]propellane with the magnesium amide reagent to produce the compound of Formula (I). The [1.1.1]propellane composition may be produced in various ways, including by traditional batch methods or by the continuous flow methods described herein, and thus may be a substantially salt-free [1.1.1] propellane composition as described herein. In various embodiments the reaction conditions are selected to minimize clogging of the continuous flow reactor by insoluble components formed during the reaction. In various embodiments, the magnesium amide reagent comprises at least one selected from $R^1R^2NMgCl$, $R^1R^2NMgBr$, $R^1R^2NMgCl \cdot LiCl$ and $R^1R^2NMgBr \cdot LiBr$.

An embodiment provides a continuous flow process for making a compound of Formula (II):

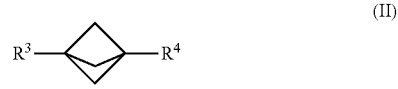

(II)

In Formula (II), $R^3$ is selected from the group consisting of an optionally substituted $C_{1-10}$ alkyl, an optionally substituted $C_{2-10}$ alkenyl, an optionally substituted $C_{3-10}$ cycloalkyl, an optionally substituted $C_{5-10}$ cycloalkenyl, an optionally substituted $C_{6-10}$ aryl, an optionally substituted heteroaryl and an optionally substituted heterocyclyl.

In Formula (II), $R^4$ is selected from the group consisting of an optionally substituted $C_{1-10}$ alkyl, an optionally substituted $C_{2-10}$ alkenyl, an optionally substituted $C_{3-10}$ cycloalkyl, an optionally substituted $C_{5-10}$ cycloalkenyl, an optionally substituted $C_{6-10}$ aryl, an optionally substituted heteroaryl and an optionally substituted heterocyclyl.

In various embodiments, the process for making the compound of Formula (II) comprises mixing a [1.1.1]propellane composition with a reagent of the formula $R^3$-$MX^1$ and a compound of the formula $R^4$—$X^2$ in the continuous flow reactor under reaction conditions selected to react the [1.1.1]propellane with the reagent of the formula $R^3$-$MX^1$ and the compound of the formula $R^4$—$X^2$ to produce the compound of Formula (II). The [1.1.1]propellane composition may be produced in various ways, including by traditional batch methods or by the continuous flow methods described herein, and thus may be a substantially salt-free [1.1.1]propellane composition as described herein. In various embodiments the reaction conditions are selected to minimize clogging of the continuous flow reactor by insoluble components formed during the reaction. In the formula $R^3$-$MX^1$ and the formula $R^4$—$X^2$, $X^1$ and $X^2$ are each independently selected from the group consisting of a halide and a pseudohalide. In the formula $R^3$-$MX^1$, M is magnesium or lithium. For example, the reagent of the formula $R^3$-$MX^1$ can be a Grignard reagent of the formula $R^3$—$MgX^1$. In various embodiments, the reaction conditions include the presence of a transition metal catalyst that is selected from the group consisting of a Pd catalyst and a Ni catalyst. For example, in various embodiments, the reaction conditions comprise mixing the transition metal catalyst in the continuous flow reactor with a previously formed mixture comprising [1.1.1]propellane, the reagent of the formula $R^3$-$MX^1$ and the compound of the formula $R^4$—$X^2$. In some embodiments, the reaction conditions include the presence of a zinc salt, such as $ZnCl_2$ and/or $ZnBr_2$. For example, in an embodiment, the reaction conditions comprise mixing the zinc salt in the continuous flow reactor with the [1.1.1]propellane, the reagent of the formula $R^3$-$MX^1$ and the compound of the formula $R^4$—$X^2$. In an embodiment, the zinc salt is mixed in after the addition of [1.1.1]propellane and the reagent of the formula $R^3$-$MX^1$. The compound of the formula $R^4$—$X^2$ and the transition metal catalyst are then added to that mixture after the zinc salt has been added.

An embodiment provides a continuous flow process for making a compound of Formula (III):

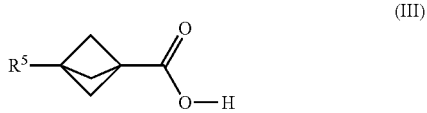

(III)

In Formula (III), $R^5$ is selected from the group consisting of an optionally substituted $C_{1-10}$ alkyl, an optionally substituted $C_{2-10}$ alkenyl, an optionally substituted $C_{3-10}$ cycloalkyl, an optionally substituted $C_{5-10}$ cycloalkenyl, an optionally substituted $C_{6-10}$ aryl, an optionally substituted heteroaryl and an optionally substituted heterocyclyl.

In various embodiments, the process for making the compound of Formula (III) comprises mixing a [1.1.1] propellane composition with carbon dioxide in the continuous flow reactor under reaction conditions selected to react the [1.1.1]propellane with the compound of the formula $R^5X^3$ and the carbon dioxide to produce a compound of Formula (III). The [1.1.1]propellane composition may be produced in various ways, including by traditional batch methods or by the continuous flow methods described herein, and thus may be a substantially salt-free [1.1.1] propellane composition as described herein. In various embodiments the reaction conditions are selected to minimize clogging of the continuous flow reactor by insoluble components formed during the reaction. In the formula $R^5X^3$, $R^5$ is as defined above and $X^3$ is selected from the group consisting of a lithium halide, a lithium pseudohalide, a zinc halide, a zinc pseudohalide, a magnesium halide, and a magnesium pseudohalide.

An embodiment provides a continuous flow process for making a compound of Formula (IV):

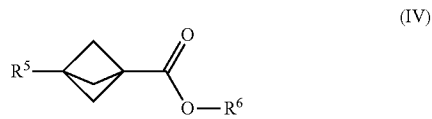

(IV)

In Formula (IV), $R^5$ is selected from the group consisting of an optionally substituted $C_{1-10}$ alkyl, an optionally substituted $C_{2-10}$ alkenyl, an optionally substituted $C_{3-10}$ cycloalkyl, an optionally substituted $C_{5-10}$ cycloalkenyl, an optionally substituted $C_{6-10}$ aryl, an optionally substituted heteroaryl and an optionally substituted heterocyclyl; and $R^6$ is an optionally substituted $C_{1-10}$ alkyl or an optionally substituted $C_{6-10}$ aryl.

In various embodiments, the process for making the compound of Formula (IV) comprises mixing a [1.1.1] propellane composition with a compound of the formula $R^5$—$X^3$ and a compound of the formula $X^4$—$CO_2R^6$ in the continuous flow reactor under reaction conditions selected to react the [1.1.1]propellane, the compound of the formula $R^5X^3$ and the compound of the formula $X^4$—$CO_2R^6$ to produce a compound of Formula (IV). The [1.1.1]propellane composition may be produced in various ways, including by traditional batch methods or by the continuous flow methods described herein, and thus may be a substantially salt-free [1.1.1]propellane composition as described herein. In various embodiments the reaction conditions are selected to minimize clogging of the continuous flow reactor by insoluble components formed during the reaction. In the formula $R^5X^3$, $R^5$ is as defined above and $X^3$ is selected from the group is selected from the group consisting of a lithium halide, a lithium pseudohalide, a magnesium halide, and a magnesium pseudohalide. In the formula $X^4$—$CO_2R^6$, $R^6$ is as defined above and $X^4$ is a halide or a pseudohalide.

An embodiment provides a continuous flow process for making a compound of Formula (V):

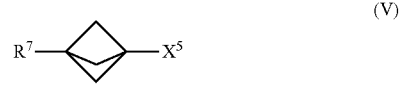

(V)

In Formula (V), $X^5$ is iodide (I) or bromide (Br) and $R^7$ is selected from the group consisting of an optionally substituted $C_{1-10}$ alkyl, an optionally substituted $C_{2-10}$ alkenyl, an optionally substituted $C_{3-10}$ cycloalkyl, an optionally substituted $C_{5-10}$ cycloalkenyl, an optionally substituted $C_{6-10}$ aryl, an optionally substituted heteroaryl and an optionally substituted heterocyclyl. In an embodiment, $X^5$ is iodide and the compound of Formula (V) is represented by the Formula (Va):

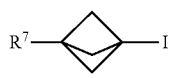

(Va)

In various embodiments, the process for making the compound of Formula (V) comprises mixing a [1.1.1]propellane composition with a compound of the formula $R^7—X^5$ in the continuous flow reactor under reaction conditions selected to react the [1.1.1]propellane with the compound of the formula $R^7—X^5$ to produce the compound of Formula (V). The [1.1.1]propellane composition may be produced in various ways, including by traditional batch methods or by the continuous flow methods described herein, and thus may be a substantially salt-free [1.1.1]propellane composition as described herein. In various embodiments the reaction conditions are selected to minimize clogging of the continuous flow reactor by insoluble components formed during the reaction. In the formula $R^7—X^5$ and the Formula (Va), the $R^7$ is as defined above with respect to the compound of Formula (V).

An embodiment provides a continuous flow process for making a compound of Formula (VI):

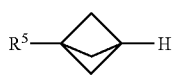

(VI)

In Formula (VI), $R^5$ is selected from the group consisting of an optionally substituted $C_{1-10}$ alkyl, an optionally substituted $C_{2-10}$ alkenyl, an optionally substituted $C_{3-10}$ cycloalkyl, an optionally substituted $C_{5-10}$ cycloalkenyl, an optionally substituted $C_{6-10}$ aryl, an optionally substituted heteroaryl and an optionally substituted heterocyclyl.

In various embodiments, the process for making the compound of Formula (VI) comprises mixing a [1.1.1]propellane composition with a compound of the formula $R^5—X^3$ and water in the continuous flow reactor under reaction conditions selected to react the [1.1.1]propellane with the compound of the formula $R^5X^3$ and the water to produce the compound of Formula (VI). The [1.1.1]propellane composition may be produced in various ways, including by traditional batch methods or by the continuous flow methods described herein, and thus may be a substantially salt-free [1.1.1]propellane composition as described herein. In various embodiments the reaction conditions are selected to minimize clogging of the continuous flow reactor by insoluble components formed during the reaction. The formula $R^5X^3$ is as defined elsewhere herein.

EXAMPLES 1-4

A tubular reactor 300 was configured with a static mixer 305, a T-mixer 310 and two stages 315, 320 as illustrated schematically in FIG. 3. A filtered stream of organometallic reagent (methyllithium (MeLi), 1.6 M in diethylether) 325 was pre-cooled and mixed with a stream of pre-cooled 1,1-dibromo-2,2-bis(chloromethyl)cyclopropane (1.0 M in 2-methyltetrahydrofuran (2-MeTHF)) using mixers 305, 310 in the tubular reactor 300 to form [1.1.1]propellane, salt, LiBr salt and methylbromide. The stoichiometry of methyllithium was 2.2 equivalents and a total flow rate of 4.4 mL/min was used. Flow rates were controlled by using syringe pumps 335, 340 to deliver the organometallic reagent and the 1,1-dibromo-2,2-bis(chloromethyl)cyclopropane. Pre-cooling prior to mixing was achieved for each of organometallic reagent and the 1,1-dibromo-2,2-bis(chloromethyl)cyclopropane using the separate 0.2 mL cooling loops 345, 350 in the first stage 315 as illustrated in FIG. 3. The mixers 305, 310 were located in the first stage 315 as illustrated in FIG. 3 and included a T-junction (T-mixer) 310 and a 29 element in-line static mixer 305 having a diameter about the same as that of the reactor tubing. The static mixer 305 includes counterhelices to achieve mixing in laminar flow. The residence time in the first stage 315 was 0.5 minutes and the residence time in the second stage 320 was 2.0 minutes. The produced [1.1.1]propellane 390 was collected at a temperature of −78° C. as indicated in FIG. 3.

The effect of reaction temperature on the yield of produced [1.1.1]propellane 390 was determined as shown in Table 2. In particular, the temperature of the first stage 315 was varied over the range of −40° C. to 0° C. while the second stage 320 was maintained at 0° C.

TABLE 2

| No. | First stage (° C.) | Yield |
|---|---|---|
| 1 | −40 | 45 |
| 2 | −20 | 57 |
| 3 | −10 | 64 |
| 4 | 0 | 62 |

The data shown in Table 2 shows that under the exemplified reaction conditions, increasing the first stage reaction temperature had a beneficial effect on yield. Some salt precipitation within the tubular reactor 300 was observed at −20° C. (Example 2), and some salt clogging issues were observed at 0° C. (Example 4). It should be noted that both stages 315, 320 were at 0° C. in Example 4, thus illustrating the effect of a single stage at 0° C. with a total residence time of 2.5 minutes and a total volume of 11 mL.

EXAMPLES 5-7

The effect of residence time on the yield of [1.1.1]propellane was determined in a tubular reactor 300 configured with a static mixer 305, a T-mixer 310 and two stages 315, 320 as illustrated in FIG. 4. The second stage residence time was varied by appending various amounts of ⅛ inch tubing to the downstream portion of the second stage. Otherwise the reactor configuration and reaction conditions were as described above for Example 3.

TABLE 3

| No. | Volume (mL) | Residence Time ($2^{nd}$) | Yield |
|---|---|---|---|
| 5 | 8.8 | 2.0 min. | 57 |
| 6 | 17.6 | 4.0 min. | 60 |
| 7 | 26.4 | 6.0 min | 52 |

The results shown in Table 3 indicate that the yield of produced [1.1.1]propellane is relatively insensitive to the second stage (0° C.) residence time under the exemplified reaction conditions. However, increased levels of clogging by precipitated salts were observed at longer residence times. Salt clogging was largely absent at the shortest residence time (Example 5).

EXAMPLES 8-9

The effect of using MeLi—LiBr complex 326 instead of MeLi as the organometallic reagent was determined using a tubular reactor 300 configured with an in-line static mixer 305, a T-mixer 310 and two stages 315, 320 as illustrated schematically in FIG. 5A. The MeLi—LiBr complex 326 used was a 1.43 M solution in diethylether that did not require pre-filtration.

For Example 8, the reactor configuration and reaction conditions were otherwise as described above for Example 3. FIG. 5A illustrates the significant reactor clogging 355 that occurred under the exemplified conditions.

For Example 9, the reactor configuration and reaction conditions were as described in Example 8, except that, as illustrated in FIG. 5B, the tubular reactor 300 did not include a pre-cooling loop for MeLi—LiBr complex 326 in the first stage 315, and a larger diameter static mixer 306 (about twice reactor tubing diameter) was used. Clogging did not occur and an 80% yield of produced [1.1.1]propellane 390 was obtained.

EXAMPLES 10-15

The effect of using phenyllithium (PhLi) instead of MeLi or MeLi—LiBr complex as the organometallic reagent was determined. The reactor configuration and reaction conditions were as described in Example 8 and illustrated schematically in FIG. 5A, except that PhLi was used as a 1.9 M solution in dibutyl ether instead of MeLi—LiBr complex 326, the second stage 320 was conducted at room temperature and the first stage 315 reaction temperature was varied as shown in Table 4. A smaller diameter static mixer 305 (about same as reactor tubing diameter) was used for Examples 10-14, and a larger diameter static mixer 305 (about twice reactor tubing diameter) was used for Example 15 along with a larger diameter T-mixer 310 (about twice reactor tubing diameter). The residence time was 0.55 minutes at the first stage and 2.2 minutes at the second stage (room temperature).

TABLE 4

| No. | First stage (° C.) | Comments |
| --- | --- | --- |
| 10 | 20 | smaller diameter mixers, salt clogging |
| 11 | 0 | smaller diameter mixers, salt clogging |
| 12 | −10 | smaller diameter mixers, salt clogging |
| 13 | −30 | smaller diameter mixers, salt clogging |
| 14 | −60 | smaller diameter mixers, PhLi clogging |
| 15 | −30 | larger diameter mixers, 58% yield of [1.1.1]propellane |

The results shown in Table 4 indicate that, as compared to MeLi or MeLi—LiBr complex, the use of PhLi has a greater tendency to result in reactor clogging under the reactor configuration and reaction conditions of Examples 10-14. However, the clogging problem was reduced in Example 15 by using the larger diameter static mixer, the larger diameter T-mixer and a first stage temperature of −30° C.

EXAMPLES 16-24

The reactor configuration and reaction conditions were as described in Example 15, except that tetrahydrofuran (THF) was used as the solvent for 1,1-dibromo-2,2-bis(chloromethyl)cyclopropane (instead of 2-MeTHF), and the first stage reaction temperature, second stage residence time, equivalents of PhLi and size of the static mixer were varied as shown in Table 5.

TABLE 5

| No. | First stage (° C.) | Residence Time ($2^{nd}$ stage, min.) | Equiv. of PhLi | Yield (%) | Comments |
| --- | --- | --- | --- | --- | --- |
| 16 | −30 | 2.2 | 2.2 | 70 | larger diameter mixer |
| 17 | −20 | 2.2 | 2.2 | — | smaller diameter mixer, clogged |
| 18 | −20 | 2.2 | 2.2 | 68 | larger diameter mixer |
| 19 | −10 | 2.2 | 2.2 | 68 | larger diameter mixer |
| 20 | −10 | 4.4 | 2.2 | 72 | larger diameter mixer |
| 21 | 0 | 2.2 | 2.2 | 74 | larger diameter mixer |
| 22 | 0 | 4.4 | 2.2 | 73 | larger diameter mixer |
| 23 | 0 | 2.2 | 2.0 | 73 | larger diameter mixer |
| 24 | 0 | 2.2 | 2.1 | 81 | larger diameter mixer |

As compared to Examples 10-15, the results shown in Table 5 indicate that higher yields of produced [1.1.1] propellane can be obtained with reduced dogging under a variety of reactor configuration and reaction conditions by using THF as the solvent for 1,1-dibromo-2,2-bis(chloromethyl)cyclopropane instead of 2-MeTHF. The highest yields of [1.1.1]propellane (81%) were obtained in Example 24, when 2.1 equivalents of PhLi was used.

EXAMPLES 25-27

The reactor configuration and reaction conditions were as described in Example 21 except that the equivalents of PhLi 327 were varied as indicated in Table 6 and the tubular reactor 300 was configured as illustrated in FIG. 6 with a larger diameter (about twice reactor tubing diameter) vertically oriented in-line static mixer 305 in the first stage (0° C.) instead of the smaller horizontally oriented in-line static mixer used in various Examples above. The results shown in Table 6 indicate that higher yields of produced [1.1.1] propellane can be obtained with reduced clogging under the exemplified reactor configuration and reaction conditions. The results also show that the highest yields of [1.1.1] propellane (86%) were obtained when 2.1 equivalents of PhLi was used (Example 27) and that the use of the larger diameter vertically oriented in-line static mixer 305 improved yields under these reaction conditions (compare Examples 24 and 27).

TABLE 6

| No. | Equiv. of PhLi | Yield (%) |
| --- | --- | --- |
| 25 | 2.2 | 69 |
| 26 | 2.1 | 86 |
| 27 | 2.0 | 72 |

EXAMPLE 28

A substantially salt-free [1.1.1]propellane composition 390 was prepared using a tubular reactor 300 configured with two static mixers 305, 306 and three stages 315, 320, 321 as illustrated schematically in FIG. 7. As compared to FIGS. 3 and 4, the configuration of FIG. 7 utilizes a larger diameter (about twice reactor tubing diameter) vertically oriented in-line static mixer 306 in the first stage 315 (-10° C.). The configuration of FIG. 7 also adds a third stage 321 (relative to those of FIGS. 3 and 4) in which the produced [1.1.1]propellane and salt are mixed with added water 360 to form a salt-containing aqueous phase, which is then separated from the produced [1.1.1]propellane via the illustrated membrane separator 365 to thereby produce a substantially salt-free [1.1.1]propellane composition 390.

FIG. 7 illustrates mixing a stream of methyllithium 325 with a stream of 1,1-dibromo-2,2-bis(chloromethyl)cyclopropane 330 to produce [1.1.1]propellane in two stages 315, 320 as generally described above in Example 3, except that the larger diameter vertically oriented static mixer 306 was used to provide mixing in the first stage. As illustrated in FIG. 7, the produced [1.1.1]propellane and salt emerging from the second stage 320 (0° C.) were mixed with water 360 in the third stage 321. A water 360 stream was pumped into the tubular reactor 300 at a flow rate of 2.0 mL/min and rapidly mixed with the emerging [1.1.1]propellane/salt stream using a static mixer 305*a* and a T-mixer 310*a*. The mixture of organic phase (containing [1.1.1]propellane) and aqueous phase (containing salt) then was separated in-line using a membrane separator 365, producing a substantially salt-free [1.1.1]propellane solution stream 390.

EXAMPLE 29

A tubular reactor was configured 300 with a static mixer 305, a T-mixer 310 and an elevated temperature stage 322 as illustrated schematically in FIG. 8. An organic stream 328 containing 3-chloro-2-(chloromethyl)prop-1-ene (1 equiv.), $CHBr_3$ (5 equiv.), 18-crown-6 (5 mol %), pinacol (8.5 mol %), and methylene chloride (4 vol.) was mixed with an aqueous 33% NaOH stream 329 at about 70° C. using mixers 305, 310 in the tubular reactor 300 to form 1,1-dibromo-2,2-bis(chloromethyl)cyclopropane 330. Flow rates were controlled by using the back pressure regulator 370 and by using the syringe pumps 335, 340 to deliver the organic and aqueous streams. The mixers 335, 340 were located in the elevated temperature stage 322 as illustrated in FIG. 8 and included a T-junction (T-mixer) 310 and a 29 element in-line static mixer 305 having a diameter about the same as that of the reactor tubing. The static mixer 305 includes counterhelices to achieve mixing of the biphasic stream in laminar flow. The residence time in the elevated temperatures stage 322 was about one hour. The yield of 1,1-dibromo-2,2-bis(chloromethyl)cyclopropane 330 was 9%.

EXAMPLES 30-38

A tubular reactor 300 was configured with a static mixer 305, a T-mixer 310 and an elevated temperature stage 323 as illustrated schematically in FIG. 9. A series of magnesium amide solutions 331 containing indoline and isopropylMgCl.LiCl ("turbo" indoline solutions) were prepared in the solvents indicated in Table 7. The effects of varying the residence time and the temperature in the elevated temperature stage 323 were evaluated. For each example, the indicated magnesium amide solution 331 was mixed with a filtered solution of [1.1.1]propellane 332 in tetrahydrofuran at about 65° C. using mixers 305, 310 in the tubular reactor 300 to form 1-(bicyclo[1.1.1]pentan-1-yl)indoline 391. Flow rates were controlled by using the back pressure regulator 370 and by using the syringe pumps 335, 340 to deliver the two reagent streams. The mixers 305, 310 were located prior to the elevated temperature stage 323 as illustrated in FIG. 9 and included a T-junction (T-mixer) 310 and a 29 element in-line static mixer 305 having a diameter about the same as that of the reactor tubing. The static mixer 305 includes counterhelices to achieve mixing of the combined stream in laminar flow. The solvent, and residence time and temperature in the elevated temperature stage 323 were varied as indicated in Table 7.

TABLE 7

| No | Solvent | Temp. (° C.) | Residence Time (min.) | Yield, % | Comments |
|---|---|---|---|---|---|
| 30 | $Bu_2O$/THF | 65 | 148 | 30 | salt clogging |
| 31 | $Bu_2O$/THF | 65 | 65 | 12 | salt clogging |
| 32 | $Bu_2O$/THF | 65 | 32 | 27 | |
| 33 | $Bu_2O$/THF | 65 | 16 | 22 | |
| 34 | THF | 75 | 16 | 20 | |
| 35 | THF | 85 | 16 | 11 | |
| 36 | THF | 95 | 16 | 19 | |
| 37 | THF | 105 | 16 | 30 | |
| 38 | THF | 105 | 8 | 14 | |

The results shown in Table 7 show that shorter residence times, higher reaction temperatures and the use of THF as a solvent resulted in less reactor clogging by salts (e.g., compare Example 30 to Example 37).

EXAMPLES 39-41

The reactor configuration and reaction conditions were as described in Examples 37-38, except that (R)—N-benzyl-1-(1H-indol-3-yl)propan-2-amine was used in place of indoline to make the magnesium amide solution and the residence time was varied as shown in Table 8.

TABLE 8

| No. | Residence Time (min.) | Yield, % |
|---|---|---|
| 39 | 32 | — |
| 40 | 16 | 38 |
| 41 | 8 | 33 |

The results shown in Table 8 show that the reactor configured as in Examples 30-38 could be used for the "turbo" amide reaction of (R)—N-benzyl-1-(1H-indol-3-yl)propan-2-amine with [1.1.1]propellane to form (R)—N-(1-(1H-indol-3-yl)propan-2-yl)-N-benzylbicyclo[1.1.1]pentan-1-amine.

EXAMPLES 42-44

A tubular reactor 300 was configured with a back-pressure regulator 370, an in-line flow infrared (IR) monitor 375 and a 365 nm LED (100 W) 380 equipped with a temperature probe 381 as illustrated schematically in FIG. 10. A distilled solution of [1.1.1]propellane in pentane/$Et_2O$ (prepared according to K. R. Mondanaro and W. P. Dailey, Org. Synth. 75 (1998) p. 98) was mixed with 1.13 molar equivalents of 2,3-butanedione to form a mixture 333 which was flowed through the reactor 300 with various residence times to determine the effect on yield of 1,3-diacetylbicyclo[1.1.1]pentane 392. The results shown in Table 9 indicate that the reaction reached steady state within about 2.5 minutes of exposure to the 365 nm LED light 380 with estimated yields of >70% based on quantitative Gas Chromatography (GC) and concentration assays.

TABLE 9

| No | Residence Time | GC Area % of [1.1.1]Propellane | GC Area % Product | Estimated Yield (%) |
|---|---|---|---|---|
| 42 | 10 | 6 | 91 | N.D. |
| 43 | 5 | 6 | 91 | 71% |
| 44 | 2.5 | 6 | 91 | 72% |

EXAMPLES 45-47

The reactor configuration and reaction conditions were as described in Examples 42-44 except that the substantially salt free [1.1.1]propellane solution was generated from either the MeLi or PhLi processes described in Examples 1-4 and 25-28 using either distillation or an aqueous quench followed by separation of the aqueous phase. The results in Table 10 show that [1.1.1]propellane that is distilled has more favorable reaction kinetics than [1.1.1]propellane isolated by aqueous workup.

TABLE 10

| Condition | 45: Non-distilled [1.1.1]Propellane | 46: Distilled [1.1.1]Propellane | 47: Non-distilled [1.1.1]Propellane |
|---|---|---|---|
| Organometallic Reagent | MeLi | PhLi | PhLi |
| Aqueous Quench | Yes | No | Yes |
| Residence Time for >90% Product Conversion (GC) | 60 min | 2.5 min | 30 min |

EXAMPLE 48

The reactor 300 configuration, as illustrated schematically in FIG. 11, was as follows: 2×0.5 mL each FEP tubing (1/16" OD, 1/32" ID) 301 for precooling of PhLi and 1,1-dibromo-2,2-bis(chloromethyl)cyclopropane streams 327, 330, followed by T-mixer 310 and a ¼" Koflo static mixer (21 elements, 7") 305. These parts were submerged in a 0° C. ice/water bath for first stage 315. Another 11 mL of ⅛" OD FEP tubing 302 in the second stage 320 of the tubular reactor 300 followed the static mixer 305 at ambient temperature of 22-23° C. The crude stream [1.1.1]propellane 390 exiting from the second stage 320 of the tubular reactor 300 was collected in a dry ice-chilled flask and then distilled via rotavap to provide substantially salt free [1.1.1]propellane. The substantially salt free [1.1.1]propellane was mixed with 2,3-butanedione to form a mixture 333 in a third stage 324. The mixture 333 was then flowed through the reactor 300 in a fourth stage 385 to produce 1,3-diacetylbicyclo[1.1.1]pentane 392 in the manner generally described above with respect to Examples 42-44. Additional experimental details are provided below.

Flow photoreactor 380: 1×100 W 365 nm UV LED chip. Light from lamp was focused on the top of a circular FEP coil reactor. A FEP reactor volume of 15 mL coil was placed in the concave side of the reflective dome (~10 cm diameter) of the photoreactor 380. Air purging was used to remove heat generated from light exposure and possible reaction exotherm. A 30 psi back-pressure regulator 370 was placed near the end of the reactor 300.

Stock Solutions A and B were prepared as follows:
Stock solution A 330: 1,1-dibromo-2,2-bis(chloromethyl)cyclopropane was dissolved to make a 1.00 M solution in THF. Coulometric Karl Fisher titration determined the solution had a water concentration of 392 ppm.

Stock solution B 327: PhLi (1.9 M) solution in Bu$_2$O

Stages 1-3 315, 320, 324: Stock solution A 330 and Stock solution B 327 were pumped at 1.8 mL/min (1.8 mmol/min, 1.00 equiv) and 2.00 mL/min (3.8 mmol/min, 2.1 equiv) respectively to the first stage 315 of the reactor 300 for 226 minutes (total of 407 mmol 1,1-dibromo-2,2-bis(chloromethyl)cyclopropane). The crude product 390 was collected in a flask chilled with dry ice pellets. The crude collected slurry material 390 was distilled in the third stage 324 using a Buchi rotavap under Buchi diaphragm pump vacuum using a dry ice condenser. The residue slurry was azeotroped twice with THF (100 mL each) and a substantially salt free [1.1.1]propellane solution was obtained (total 632 g or 707 mL).

Stage 4 385: The [1.1.1]propellane solution (707 mL, 0.6M) from the third stage 324 was mixed with 2,3-butanedione (50.3 g, 584 mmol, 1.4 equiv) and diluted with THF (364 mL) to make a mixture 333 having a volume of 1120 mL (~0.36 M [1.1.1]propellane theoretical concentration).

The mixture 333 was pumped at 6 mL/min through the photoreactor 380 with a residence time of 2.5 min. The total run time was approximately 3 h 15 min. OC assay showed >98% conversion by area. The collected solution 392 was concentrated to 50-100 mL and settled to crystallize the product at RT. Hexanes (~400 mL) was added to drive crystallization. A first crop of 25 g product was collected. The mother liquor was concentrated and further crystallized out twice from TBME/hexane (50/50) at −78° C. to give another 11 g of product. A total of 36 g of 1,3-diacetylbicyclo[1.1.1]pentane was obtained (58% isolated yield over 2 steps, 12 g/h productivity with a 100 W lamp or 120 g/kWh).

What is claimed is:

1. A continuous flow process for making a bicyclic compound, comprising mixing 1,1-dibromo-2,2-bis(chloromethyl)cyclopropane with an organometallic reagent in a continuous flow reactor to thereby form a reagent mixture; and mixing the reagent mixture with a static mixer in the continuous flow reactor under first reaction conditions selected to react the 1,1-dibromo-2,2-bis(chloromethyl)cyclopropane with the organometallic reagent to produce [1.1.1]propellane and a salt; wherein the static mixer provides a mixing rate that is effective to minimize clogging of the continuous flow reactor by the salt.

2. The process of claim 1, wherein the organometallic reagent is selected from the group consisting of n-butyllithium, methyllithium, methyllithium lithium bromide complex, and phenyllithium.

3. The process of claim 1, wherein the salt comprises LiCl, LiBr, or both.

4. The process of claim 1, wherein the first reaction conditions comprise mixing a solvent with the 1,1-dibromo-2,2-bis(chloromethyl)cyclopropane and the organometallic reagent in the continuous flow reactor, wherein the solvent is selected from the group consisting of diethylether, diethoxymethane, dibutylether, methyl tert-butyl ether, tetrahydrofuran, 2-methyltetrahydrofuran and mixtures thereof.

5. The process of claim 1, wherein the continuous flow reactor comprises a first stage and a second stage.

6. The process of claim 5, wherein the reaction conditions further comprise a first reaction temperature in the range of about −50° C. to about 0° C. during the first stage.

7. The process of claim 6, wherein the reaction conditions further comprise a second reaction temperature in the range of about −10° C. to about 25° C. during the second stage.

8. The process of claim 5, wherein the continuous flow reactor further comprises a third stage.

9. The process of claim 8, wherein the third stage comprises mixing an aqueous composition with the produced [1.1.1]propellane and the salt in the continuous flow reactor to form a salt-containing aqueous phase.

10. The process of claim 9, wherein the aqueous composition comprises a buffer.

11. The process of claim 9, further comprising separating the salt-containing aqueous phase from the produced [1.1.1]propellane to thereby produce a [1.1.1]propellane composition.

12. The process of claim 8, wherein the third stage comprises distilling the produced [1.1.1]propellane to thereby produce a [1.1.1]propellane composition.

13. The process of claim 11, further comprising mixing the [1.1.1]propellane composition with 2,3-butanedione in the continuous flow reactor under second reaction conditions selected to react the produced [1.1.1]propellane with the 2,3-butanedione to produce 1,3-diacetylbicyclo[1.1.1]pentane, wherein the second reaction conditions comprise exposing the produced [1.1.1]propellane and the 2,3-butanedione to a light source.

14. The process of claim 13, wherein the light source is a source of radiation in the range of about 350 nm to about 380 nm.

15. The process of claim 13, wherein the light source comprises a light emitting diode.

16. The process of claim 1, further comprising mixing the produced [1.1.1]propellane with a magnesium amide reagent in the continuous flow reactor under second reaction conditions selected to react the produced [1.1.1]propellane with the magnesium amide reagent to produce a compound of Formula (I):

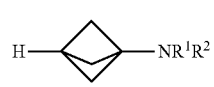

(I)

wherein $R^1$ and $R^2$ are each individually selected from the group consisting of hydrogen, an optionally substituted $C_{1-10}$ alkyl, an optionally substituted $C_{3-10}$ monocyclic cycloalkyl, an optionally substituted $C_{6-10}$ aryl, an optionally substituted ($C_{6-10}$ aryl)alkyl, an optionally substituted $C_{5-10}$ heteroaryl, an optionally substituted ($C_{5-10}$ heteroaryl)alkyl, phenyl and benzyl; or $R^1$, $R^2$ and the nitrogen to which they are attached together form an optionally substituted heterocyclyl.

17. The process of claim 16, wherein the magnesium amide reagent comprises at least one selected from $R^1R^2NMgCl$, $R^1R^2NMgBr$, $R^1R^2NMgCl.LiCl$ and $R^1R^2NMgBr.LiBr$.

18. The process of claim 1, further comprising mixing the produced [1.1.1]propellane with a reagent of the formula $R^3$-$MX^1$ and a compound of the formula $R^4$—$X^{22}$ in the continuous flow reactor under second reaction conditions selected to react the produced [1.1.1]propellane with the reagent of the formula $R^3$-$MX^1$ and the compound of the formula $R^4$—$X^2$ to produce a compound of Formula (II):

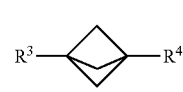

(II)

wherein $R^3$ is selected from the group consisting of an optionally substituted $C_{1-10}$ alkyl, an optionally substituted $C_{2-10}$ alkenyl, an optionally substituted $C_{3-10}$ cycloalkyl, an optionally substituted $C_{5-10}$ cycloalkenyl, an optionally substituted $C_{6-10}$ aryl, an optionally substituted heteroaryl and an optionally substituted heterocyclyl;

wherein $R^4$ is selected from the group consisting of an optionally substituted $C_{1-10}$ alkyl, an optionally substituted $C_{2-10}$ alkenyl, an optionally substituted $C_{3-10}$ cycloalkyl, an optionally substituted $C_{5-10}$ cycloalkenyl, an optionally substituted $C_{6-10}$ aryl, an optionally substituted heteroaryl and an optionally substituted heterocyclyl wherein $X^1$ and $X^2$ are each independently selected from the group consisting of a halide and a pseudohalide;

wherein M is magnesium or lithium; and wherein the second reaction conditions comprise the presence of a transition metal catalyst that is selected from the group consisting of a Pd catalyst and a Ni catalyst.

19. The process of claim 18, wherein the second reaction conditions comprise mixing a zinc salt with the produced [1.1.1]propellane, the reagent of the formula $R^3$-$MX^1$ and the compound of the formula $R^4$—$X^2$ in the continuous flow reactor prior to mixing with the transition metal catalyst.

20. The process of claim 1, further comprising mixing the produced [1.1.1]propellane with a compound of the formula $R^5$—$X^3$ and carbon dioxide in the continuous flow reactor under second reaction conditions selected to react the produced [1.1.1]propellane with the compound of the formula $R^5X^3$ and the carbon dioxide to produce a compound of Formula (III):

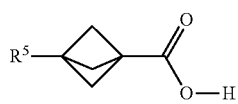

(III)

wherein $R^5$ is selected from the group consisting of an optionally substituted $C_{1-10}$ alkyl, an optionally substituted $C_{2-10}$ alkenyl, an optionally substituted $C_{3-10}$ cycloalkyl, an optionally substituted $C_{5-10}$ cycloalkenyl, an optionally substituted $C_{6-10}$ aryl, an optionally substituted heteroaryl and an optionally substituted heterocyclyl; and wherein $X^3$ is selected from the group consisting of a lithium halide, a lithium pseudohalide, a zinc halide, a zinc pseudohalide, a magnesium halide, and a magnesium pseudohalide.

21. The process of claim 1, further comprising mixing the produced [1.1.1]propellane with a compound of the formula $R^5—X^3$ and a compound of the formula $X^4—CO_2R^6$ in the continuous flow reactor under second reaction conditions selected to react the produced [1.1.1]propellane with the compound of the formula $R^5X^3$ and the compound of the formula $X^4—CO_2R^6$ to produce a compound of Formula (IV):

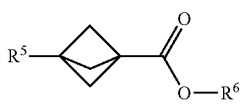

(IV)

wherein $R^5$ is selected from the group consisting of an optionally substituted $C_{1-10}$ alkyl, an optionally substituted $C_{2-10}$ alkenyl, an optionally substituted $C_{3-10}$ cycloalkyl, an optionally substituted $C_{5-10}$ cycloalkenyl, an optionally substituted aryl, an optionally substituted heteroaryl and an optionally substituted heterocyclyl;

wherein $R^6$ is an optionally substituted $C_{1-10}$ alkyl or an optionally substituted $C_{6-10}$ aryl;

wherein $X^3$ is selected from the group consisting of a lithium halide, a lithium pseudohalide, a magnesium halide, and a magnesium pseudohalide; and wherein $X^4$ is a halide or a pseudohalide.

22. The process of claim 1, further comprising mixing the produced [1.1.1]propellane with a compound of the formula $R^7—X^5$ in the continuous flow reactor under second reaction conditions selected to react the produced [1.1.1]propellane with the compound of the formula $R^7—X^5$ to produce a compound of Formula (V):

(V)

wherein $X^5$ is iodide (I) or bromide (Br) and $R^7$ is selected from the group consisting of an optionally substituted $C_{1-10}$ alkyl, an optionally substituted $C_{2-10}$ alkenyl, an optionally substituted $C_{3-10}$ cycloalkyl, an optionally substituted $C_{5-10}$ cycloalkenyl, an optionally substituted $C_{6-10}$ aryl, an optionally substituted heteroaryl and an optionally substituted heterocyclyl.

23. The process of claim 1, further comprising mixing the produced [1.1.1]propellane with a compound of the formula $R^5X^3$ and water in the continuous flow reactor under second reaction conditions selected to react the produced [1.1.1]propellane with the compound of the formula $R^5X^3$ and the water to produce a compound of Formula (VI):

(VI)

wherein $R^5$ is selected from the group consisting of an optionally substituted $C_{1-10}$ alkyl, an optionally substituted $C_{2-10}$ alkenyl, an optionally substituted $C_{3-10}$ cycloalkyl, an optionally substituted $C_{5-10}$ cycloalkenyl, an optionally substituted $C_{6-10}$ aryl, an optionally substituted heteroaryl and an optionally substituted heterocyclyl; and wherein $X^3$ is selected from the group consisting of a lithium halide, a lithium pseudohalide, a zinc halide, a zinc pseudohalide, a magnesium halide, and a magnesium pseudohalide.

24. The process of claim 1, further comprising mixing 3-chloro-2-(chloromethyl)prop-1-ene with $CHBr_3$ in the continuous flow reactor under reaction conditions selected to produce the 1,1-dibromo-2,2-bis(chloromethyl)cyclopropane.

25. The process of claim 24, wherein the reaction conditions comprise mixing an aqueous base with the 3-chloro-2-(chloromethyl)prop-1-ene and the $CHBr_3$ in the continuous flow reactor.

26. The process of claim 25, wherein the aqueous base is aqueous NaOH, aqueous KOH or a mixture thereof.

27. The process of claim 24, wherein the reaction conditions comprise phase transfer conditions.

28. The process of claim 27, wherein the phase transfer conditions comprise a catalytically effective amount of a phase transfer catalyst selected from pinacol, a crown ether and a mixture thereof.

29. The process of claim 28, wherein the crown ether is 18-crown-6.

30. The process of claim 24, wherein the reaction conditions comprise mixing an organic solvent, an aqueous base, and a phase transfer catalyst with the 3-chloro-2-(chloromethyl)prop-1-ene and the $CHBr_3$ in the continuous flow reactor under phase transfer reaction conditions.

31. The process of claim 1, wherein the static mixer has a diameter that is larger than a diameter of a reactor tubing of the continuous flow reactor to which the static mixer is attached.

* * * * *

UNITED STATES PATENT AND TRADEMARK OFFICE
CERTIFICATE OF CORRECTION

PATENT NO. : 11,339,103 B2
APPLICATION NO. : 16/644640
DATED : May 24, 2022
INVENTOR(S) : Joseph Robert Pinchman Page 1 of 2

It is certified that error appears in the above-identified patent and that said Letters Patent is hereby corrected as shown below:

On the Title Page

Page 2, Column 2 (Other Publications), Line 33, delete "poropellane" and insert -- propellane --.

In the Drawings

Sheet 10 of 13 (Reference Numeral 328), (FIG. 8), Line 1, delete "1ene" and insert -- 1-ene --.

In the Specification

Column 2, Line 57, delete "[1.1.1.1]" and insert -- [1.1.1] --.

Column 3, Line 38, delete "$R^5$—$X^3$" and insert -- $R^5X^3$ --.

Column 4, Line 27, delete "bi s" and insert -- bis --.

Column 7, Line 51-52, delete "to the rings. For example, in the following structure, rings A and B are fused" and insert the same on Column 7, Line 50, as a continuation of the same paragraph.

Column 7, Line 54-57 (approx.), delete " 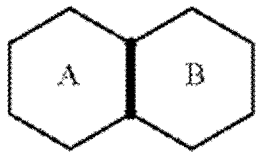 " and insert -- 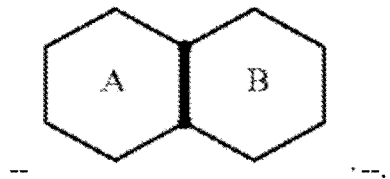 --.

Signed and Sealed this
Sixth Day of September, 2022

Katherine Kelly Vidal
*Director of the United States Patent and Trademark Office*

CERTIFICATE OF CORRECTION (continued)
U.S. Pat. No. 11,339,103 B2

Column 8, Line 55, delete "benzoisoxazole," and insert -- benzisoxazole, --.

Column 11, Line 50, delete "[ 1.1.1]" and insert -- [1.1.1] --.

Column 12, Line 32, delete "$CH_2C_{12}$" and insert -- $CH_2Cl_2$ --.

Column 15, Line 38, delete "hatch" and insert -- batch --.

Column 19, Line 63, before "salt," insert -- LiCl --.

Column 22, Line 33, delete "dogging" and insert -- clogging --.

Column 23, Line 56, delete "9%." and insert -- ~9%. --.

Column 24, Line 24, delete "THE" and insert -- THF --.

Column 24, Line 25, delete "THE" and insert -- THF --.

Column 24, Line 26, delete "THE" and insert -- THF --.

Column 24, Line 27, delete "THE" and insert -- THF --.

Column 24, Line 28, delete "THE" and insert -- THF --.

Column 26, Line 39, delete "OC" and insert -- GC --.

Column 28, Line 3-4, delete "$R^1R^2NMgCl.LiCl$ and $R^1R^2NMgBr.LiBr$" and insert -- $R^1R^2NMgCl \cdot LiCl$ and $R^1R^2NMgBr \cdot LiBr$ --.

In the Claims

Column 28, Line 7, Claim 18, delete "$R^4-X^{22}$" and insert -- $R^4-X^2$ --.